(12) United States Patent
Meneyrol et al.

(10) Patent No.: US 9,878,990 B2
(45) Date of Patent: Jan. 30, 2018

(54) BENZYLHYDROXIDE DERIVATIVES, PREPARATION THEREOF AND THERAPEUTIC USE THEREOF

(71) Applicant: SANOFI, Paris (FR)

(72) Inventors: Jérôme Meneyrol, Paris (FR); Nathalie Alet, Paris (FR); Guillaume Barre, Paris (FR); Tristan Rousseaux, Paris (FR); Valérie Vin, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 15/523,174

(22) PCT Filed: Oct. 29, 2015

(86) PCT No.: PCT/EP2015/075112
§ 371 (c)(1),
(2) Date: Apr. 28, 2017

(87) PCT Pub. No.: WO2016/066742
PCT Pub. Date: May 6, 2016

(65) Prior Publication Data
US 2017/0313674 A1    Nov. 2, 2017

(30) Foreign Application Priority Data
Oct. 30, 2014    (EP) .................................... 14306747

(51) Int. Cl.
| | |
|---|---|
| C07D 233/56 | (2006.01) |
| C07D 277/22 | (2006.01) |
| C07D 271/06 | (2006.01) |
| C07D 263/32 | (2006.01) |
| C07D 285/08 | (2006.01) |
| C07D 333/16 | (2006.01) |
| A61K 31/375 | (2006.01) |
| A61K 31/4164 | (2006.01) |
| A61P 35/00 | (2006.01) |
| C07D 233/64 | (2006.01) |

(52) U.S. Cl.
CPC ......... *C07D 333/16* (2013.01); *C07D 233/64* (2013.01); *C07D 263/32* (2013.01); *C07D 271/06* (2013.01); *C07D 285/08* (2013.01)

(58) Field of Classification Search
None
See application file for complete search history.

(56) References Cited

FOREIGN PATENT DOCUMENTS

| WO | WO-2010/054764 A1 | 5/2010 |
| WO | WO-2014/076439 A1 | 5/2014 |

OTHER PUBLICATIONS

Hanahan, D. et al. (Mar. 4, 2011). "Hallmarks of Cancer: The Next Generation," *Cell* 144:646-674.
Hong, S.S. et al. (2004). "HIF-1 α: A Valid Therapeutic Target for Tumor Therapy," *Cancer Research and Treatment* 36(6):343-353.
Huang, K. et al. (Jun. 5, 2009). "Spiroborate Ester-Mediated Asymmetric Synthesis of β-Hydroxy Ethers and its Conversion to Highly Enantiopure β-Amino Ethers," *J Org Chem.* 74(11)-4195-4202.
Li, N. et al. (Mar. 7, 2003). "Mitochondrial Complex I Inhibitor Rotenone Induces Apoptosis through Enhancing Mitochondrial Reactive Oxygen Species Production," *The Journal of Biological Chemistry* 278 (10):8516-8525.
Liao, D. et al. (Jan. 15, 2007). "Hypoxia-Inducible Factor-1α Is a Key Regulator of Metastasis in a Transgenic Model of Cancer Initiation and Progression," *Cancer Research* 67(2):563-572.
Semenza, G.L. (Feb. 2010; e-published on Nov. 26, 2009). "HIF-1 Upstream and Downstream of Cancer Metabolism," *Curr Opin Genet Dev.* 20(1):51-56.
Wenger, R.H. (Mar. 23, 2000). "Mammalian Oxygen Sensing, Signalling and Gene Regulation," *The Journal of Experimental Biology* 203:1253-1263.
Wutz et al. (2007). *Greene's Protective Groups in Organic Synthesis*, Fourth Edition, John Wiley & Sons, Inc., New York, Table of contents only, twenty seven pages.
International Search Report dated Dec. 8, 2015, for International Application No. PCT/EP2015/075112, filed on Oct. 29, 2015, three pages.
Written Opinion of the International Searching Authority dated Dec. 8, 2015, for International Application No. PCT/EP2015/075112, filed on Oct. 29, 2015, four pages.

*Primary Examiner* — Alicia L Otton
(74) *Attorney, Agent, or Firm* — Morrison & Foerster LLP

(57) ABSTRACT

The invention relates to benzylhydroxyde derivatives of formula (I): The invention also relates to the preparation and the therapeutic use of the compounds of formula (I).

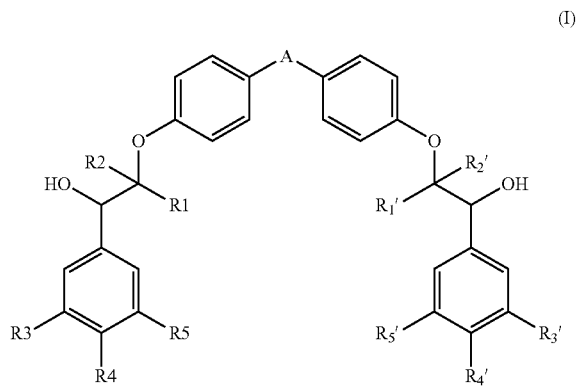

23 Claims, No Drawings

BENZYLHYDROXIDE DERIVATIVES, PREPARATION THEREOF AND THERAPEUTIC USE THEREOF

CROSS REFERENCE TO RELATED APPLICATIONS

This application is a National Phase application under 35 U.S.C. § 371 of International Application No. PCT/EP2015/075112, filed Oct. 29, 2015, which claims priority benefit to European Application No. 14306747.8, filed Oct. 30, 2014, the disclosures of each of which are herein incorporated by reference in their entireties.

The present invention relates to benzylhydroxyde derivatives, to their preparation and to their therapeutic use.

The compounds according to the present invention are direct safe inhibitors of the complex 1 of the mitochondrial respiratory chain and indirect inhibitors of Hypoxia Inducible Factor (HIF-1) stabilization under hypoxic stress.

Mitochondrial complex I, also called NADH: Ubiquinone oxidoreductase, is a key component of the respiratory chain. Mitochondrial complex 1 contributes to the formation of membrane potential coupled to ATP synthesis at the origin of the energy supporting cellular processes. Composed of 45 subunits coded by both the genomic and mitochondrial DNAs, the complex 1 is present in the inner mitochondrial membrane of all the mammalian cells and is the main consumer of the NADH generated in the Krebs cycle and the regulator of NADH/NAD+ homeostasis in the cell.

Due to its function, the complex 1 is responsible for the indirect modulation of many different cellular metabolites (AMP/ATP and NADH/NAD+ ratios, alpha ketoglutarate, succinate and oxygen for examples) involved in the pathways which support cellular proliferation, growth and adaptation under specific stress.

Under oxidative stress, the mitochondrial complex 1 participates as the major source of the radical oxygen species (ROS) production in the mitochondrial respiratory chain to the induction of apoptosis (Li et al, 2003).

Through the indirect modulation of alpha ketoglutarate, succinate and oxygen concentrations, the mitochondrial complex 1 also participates to the regulation of prolyl hydroxylase activity (PHD) which leads to the degradation of hypoxia inducible factor (HIF) under normoxia. Under hypoxia or dysfunction of some enzymes of the TCA (succinate dehydrogenase, fumarate hydratase), PHD is inhibited, HIF-1a stabilized and translocated to the nucleus. HIF1a acts as a transcription factor which leads to the upregulation of target genes involved in many aspects of cancer progression, angiogenesis, cell survival, glucose metabolism and invasion. More than 70 putative HIF-1 target genes have currently been identified (S. S. Hong & al., 2004).

In the 1920s, Otto Warburg demonstrated tumor cells present a specific metabolism compared to primary cells: an increase of cellular glucose avidity (Warburg effect) under normoxic conditions (aerobic glycolysis). Since few years, metabolism deregulation has finally been defined as an emerging hallmark of cancer (Hanahan et al. (2011) Cell, 144). And this observation has been even more translated to clinics where aggressive tumors are nowadays commonly diagnosed thanks to their glucose avidity (FDG Petscan). Understanding metabolic adaptation under stress and developing strategy to target specific tumor cell metabolism appears now an evidence for the community.

Many cancers demonstrate a glycolytic shift (Warburg effect) which correlates with tumor aggressiveness and poor prognostic. It is for example the case of most of the glioblastoma or triple negative breast cancers, metastatic head and neck cancers or metastatic melanomas. On the other hand, some tumors depend on oxidative phosphorylation metabolism (OXPHOS, mitochondria) to grow. Tumors relying on pyruvate, glutamine or lipids to grow may depend on OXPHOS metabolism to support ATP generation, oxidoreduction homeostasis and aminoacids providing. For example, hormono-dependent breast tumors, some lung tumors, hepatocarcinomas, gastrointestinal tumors, overexpressing c-Myc tumors such as some lymphomas should almost be considered as OXPHOS depending tumors. Furthermore, new evidence support the fact that treatment resistance occurring after some "targeted therapies" targeting pathways which support glycolytic metabolism can be reached by a shift of tumor metabolism to OXPHOS dependency. Researches are performed to identify some new ways to diagnose those tumor types through specific innovative biopsies respiration assay, or specific development of PET-Scan biomarkers as $^{18}$F-Glutamine or $^{11}$C-acetate for example.

Beyond its major role in supporting OXPHOS tumors metabolism, the complex 1 participates to the development of the tumor toward the establishment of an aggressive pattern triggered by HIF1 stabilization under hypoxic conditions. It is clear today that modulation of mitochondrial function activity leads to modulation of HIF1 stabilization: inhibition of complex 1 reducing HIF-1a stabilization under hypoxia although complex 2 (succinate dehydrogenase) inhibition leading to increased HIF-1a stabilization under normoxia (SDH or FH mutations leads to cancer development through HIF stabilization). Multiple enzymes responsible for shifting the metabolism toward anaerobic glycolysis (Wenger, R. H., 2000), implicated in the regulation of intracellular pH, tumor invasiveness and metastasis are directly controlled by HIF-1a. And increased HIF-1a levels in diagnostic tumor biopsies are associated with increased risk of mortality in cancers of bladder, brain, breast, colon, cervix, endometrium, head/neck, lung, ovary, pancreas, prostate, rectum and stomach. Furthermore, experimental manipulations that increase HIF-1a expression result in increased tumor growth, whereas loss of HIF activity results in decreased tumor growth (Semenza, G. L., 2010). In the same way, HIF-1a null tumors exhibit retarded growth and reduced pulmonary metastasis (Liao D., et al., 2007). Preventing OXPHOS dependent growth, metabolic adaptation and tumor vascularization through HIF1a destabilization and inducing apoptosis with specific and safe mitochondrial complex 1 inhibitor appears as a consequence to be a new way to address those tumors.

The present invention provides the compounds of the formula (I):

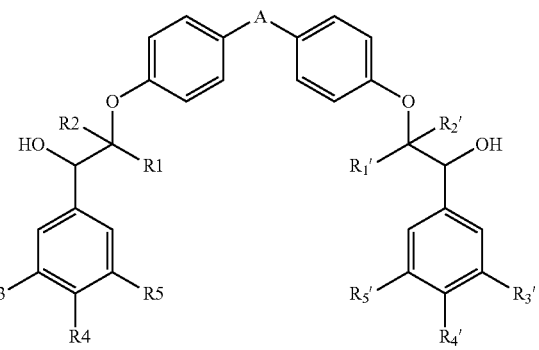

wherein
A represents a 5-membered heteroaryl group comprising between 1 and 3 heteroatoms, at least one heteroatom being selected from a sulfur atom and a nitrogen atom, A being unsubstituted or substituted with one or more (C1-C4)alkyl groups, each (C1-C4) alkyl group unsubstituted or substituted with a heterocyclyl group,
each of R1, R2, R1' and R2' independently represents a hydrogen atom or a (C1-C4 alkyl) group, and
each of R3, R4, R5, R3', R4' and R5' is independently selected from a hydrogen atom, a halogen atom, an —O-fluoromethyl group and a (C1-C4)alkoxy group, wherein at least one from R3, R4 and R5 represents a (C1-C4)alkoxy group and at least one from R3', R4' and R5' represents a (C1-C4)alkoxy group,
in the form of a base, enantiomers, diastereoisomers including racemic mixture, and addition salt with an acid.

The compounds of formula (I) may contain one or more asymmetric carbon atoms. They may therefore exist in the form of enantiomers or diastereoisomers. These enantiomers and diastereoisomers, and also mixtures thereof, including the racemic mixtures, form part of the invention.

Diastereomers can be separated into the individual isomers, for example, by chromatography. Racemates can be separated into the two enantiomers by customary methods, for example by chromatography on chiral phases.

The compounds of formula (I) may exist in the form of bases or addition salts with acids. Such addition salts form part of the invention.

These salts may be prepared with pharmaceutically acceptable acids, although the salts of other acids useful, for example, for purifying or isolating compounds of formula (I) also form part of the invention.

In the context of the present invention, certain terms have the following definitions:
a halogen atom: a fluorine, a chlorine, a bromine or an iodine;
an alkyl group: a linear or branched saturated hydrocarbon group. Examples include the groups methyl, ethyl, propyl, isopropyl, butyl, isobutyl, tert-butyl, etc.;
a fluoroalkyl group: an alkyl group in which one or more hydrogen atoms have been substituted by a fluorine atom;
an alkoxy group: an —O-alkyl radical in which the alkyl group is as defined above;
a heteroaryl group: a cyclic aromatic group containing between 2 and 4 carbon atoms and containing between 1 and 3 heteroatoms, such as nitrogen, oxygen or sulphur. Examples of heteroaryl groups include oxazolyl, thiazol, thienyl, oxadiazolyl, thiadiazolyl or indolyl groups;
a heterocyclyl group: a saturated cyclic group containing between 5 and 10 carbon atoms and containing between 1 and 3 heteroatoms, such as nitrogen, oxygen or sulphur. Examples of heterocyclyl groups include morpholine groups.

Among the compounds of formula (I) that are subject matter of the invention, a first group of compounds is composed of the compounds for which A comprises an oxygen atom.

Among the compounds of formula (I) that are subject matter of the invention, a second group of compounds is composed of the compounds for which A represents an oxazolyl, thiazol, thienyl, oxadiazolyl, thiadiazolyl or imidazolyl group.

Among the compounds of formula (I) that are subject matter of the invention, a third group of compounds is composed of the compounds for which A is unsubstituted.

Among the compounds of formula (I) that are subject matter of the invention, a fourth group of compounds is composed of the compounds for which that A is substituted with one or more methyl groups.

Among the compounds of formula (I) that are subject matter of the invention, a fifth group of compounds is composed of the compounds for which each of R1, R2, R1' and R2' represents a hydrogen atom or a methyl group.

Among the compounds of formula (I) that are subject matter of the invention, a sixth group of compounds is composed of the compounds for which at least two from R3, R4 and R5 represent —OCH$_3$ and at least two from R3', R4' and R5' represent —OCH$_3$.

In particular, among the compounds the sixth group of compounds, mention may be made of the compounds for which two from R3, R4 and R5 represent —OCH$_3$ and two from R3', R4' and R5' represent —OCH$_3$.

Among the compounds of formula (I) that are subject matter of the invention, a seventh group of compounds is composed of the compounds for which at least one of R3, R4, R5, R3', R4' and R5' represents —OCHF$_2$.

Among the compounds of formula (I) that are subject matter of the invention, an eighth group of compounds is composed of the compounds for which R1=R1', R2=R2', R3=R3', R4=R4' and R5=R5'.

Among the compounds of formula (I) that are subject matter of the invention, mention may be made in particular of the following compounds:
1-(3,4-dimethoxyphenyl)-2-[4-[2-[4-[2-(3,4-dimethoxyphenyl)-2-hydroxy-ethoxy]phenyl]-5-methyl-oxazol-4-yl]phenoxy]ethanol;
1-(3,4-dimethoxyphenyl)-2-[4-[2-[4-[2-(3,4-dimethoxyphenyl)-2-hydroxy-1,1-dimethyl-ethoxy]phenyl]-5-methyl-oxazol-4-yl]phenoxy]-2-methyl-propan-1-ol;
1-(3,4-dimethoxyphenyl)-2-[4-[2-[4-[2-(3,4-dimethoxyphenyl)-2-hydroxy-ethoxy]phenyl]-4-methyl-oxazol-5-yl]phenoxy]ethanol;
1-(3,4-dimethoxyphenyl)-2-[4-[2-[4-[2-(3,4-dimethoxyphenyl)-2-hydroxy-1,1-dimethyl-ethoxy]phenyl]-5-methyl-thiazol-4-yl]phenoxy]-2-methyl-propan-1-ol;
1-(3,4-dimethoxyphenyl)-2-[4-[2-[4-[2-(3,4-dimethoxyphenyl)-2-hydroxy-ethoxy]phenyl]-5-methyl-thiazol-4-yl]phenoxy]ethanol;
1-(3,4-dimethoxyphenyl)-2-[4-[2-[4-[2-(3,4-dimethoxyphenyl)-2-hydroxy-1,1-dimethyl-ethoxy]phenyl]-5-methyl-thiazol-4-yl]phenoxy]-2-methyl-propan-1-ol;
1-(3,4-dimethoxyphenyl)-2-[4-[2-[4-[2-(3,4-dimethoxyphenyl)-2-hydroxy-ethoxy]phenyl]-5-methyl-thiazol-4-yl]phenoxy]ethanol;
1-(3,4-dimethoxyphenyl)-2-[4-[2-[4-[2-(3,4-dimethoxyphenyl)-2-hydroxy-1-methyl-ethoxy]phenyl]oxazol-4-yl]phenoxy]propan-1-ol;
1-(3,4-dimethoxyphenyl)-2-[4-[2-[4-[2-(3,4-dimethoxyphenyl)-2-hydroxy-ethoxy]phenyl]oxazol-4-yl]phenoxy]ethanol;
1-(4-chloro-3-methoxy-phenyl)-2-[4-[2-[4-[2-(4-chloro-3-methoxy-phenyl)-2-hydroxy-ethoxy]phenyl]oxazol-4-yl]phenoxy]ethanol;
1-(4-fluoro-3-methoxy-phenyl)-2-[4-[2-[4-[2-(4-fluoro-3-methoxy-phenyl)-2-hydroxy-ethoxy]phenyl]oxazol-4-yl]phenoxy]ethanol;
1-(3-fluoro-4-methoxy-phenyl)-2-[4-[2-[4-[2-(3-fluoro-4-methoxy-phenyl)-2-hydroxy-ethoxy]phenyl]oxazol-4-yl]phenoxy]ethanol;
1-(3,4-dimethoxyphenyl)-2-[4-[2-[4-[2-(3,4-dimethoxyphenyl)-2-hydroxy-1,1-dimethyl-ethoxy]phenyl]oxazol-4-yl]phenoxy]-2-methyl-propan-1-ol;

2-[4-[2-[4-[2-hydroxy-2-(3,4,5-trimethoxyphenyl)ethoxy]
phenyl]oxazol-4-yl]phenoxy]-1-(3,4,5-trimethoxyphenyl)ethanol;

1-(3,4-dimethoxyphenyl)-2-[4-[2-[4-[2-(3,4-dimethoxyphenyl)-2-hydroxy-ethoxy]phenyl]thiazol-4-yl]phenoxy]
ethanol;

1-(3,4-dimethoxyphenyl)-2-[4-[2-[4-[2-(3,4-dimethoxyphenyl)-2-hydroxy-1,1-dimethyl-ethoxy]phenyl]thiazol-4-yl]phenoxy]-2-methyl-propan-1-ol;

1-(3,4-dimethoxyphenyl)-2-[4-[2-[4-[2-(3,4-dimethoxyphenyl)-2-hydroxy-1-methyl-ethoxy]phenyl]thiazol-4-yl]phenoxy]propan-1-ol;

1-(3,4-dimethoxyphenyl)-2-[4-[2-[4-[2-(3,4-dimethoxyphenyl)-2-hydroxy-ethoxy]phenyl]thiazol-4-yl]phenoxy]
ethanol;

1-(3,4-dimethoxyphenyl)-2-[4-[4-[4-[2-(3,4-dimethoxyphenyl)-2-hydroxy-ethoxy]phenyl]thiazol-2-yl]phenoxy]-2-methyl-propan-1-ol;

1-(3,4-dimethoxyphenyl)-2-[4-[2-[4-[2-(3,4-dimethoxyphenyl)-2-hydroxy-ethoxy]phenyl]thiazol-4-yl]phenoxy]-2-methyl-propan-1-ol;

1-(3,4-dimethoxyphenyl)-2-[4-[5-[4-[2-(3,4-dimethoxyphenyl)-2-hydroxy-1,1-dimethyl-ethoxy]phenyl]-3-thienyl]
phenoxy]-2-methyl-propan-1-ol;

1-(3,4-dimethoxyphenyl)-2-[4-[5-[4-[2-(3,4-dimethoxyphenyl)-2-hydroxy-ethoxy]phenyl]-3-thienyl]phenoxy]ethanol;

1-(3,4-dimethoxyphenyl)-2-[4-[5-[4-[2-(3,4-dimethoxyphenyl)-2-hydroxy-ethoxy]phenyl]-1,2,4-oxadiazol-3-yl]
phenoxy]ethanol;

1-(3,4-dimethoxyphenyl)-2-[4-[5-[4-[2-(3,4-dimethoxyphenyl)-2-hydroxy-1,1-dimethyl-ethoxy]phenyl]-1,2,4-oxadiazol-3-yl]phenoxy]-2-methyl-propan-1-ol;

1-(3,4-dimethoxyphenyl)-2-[4-[5-[4-[2-(3,4-dimethoxyphenyl)-2-hydroxy-1-methyl-ethoxy]phenyl]-1,2,4-thiadiazol-3-yl]phenoxy]propan-1-ol;

1-(3,4-dimethoxyphenyl)-2-[4-[5-[4-[2-(3,4-dimethoxyphenyl)-2-hydroxy-ethoxy]phenyl]-1,2,4-thiadiazol-3-yl]
phenoxy]ethanol;

1-(3,4-dimethoxyphenyl)-2-[4-[5-[4-[2-(3,4-dimethoxyphenyl)-2-hydroxy-1,1-dimethyl-ethoxy]phenyl]-1,2,4-thiadiazol-3-yl]phenoxy]-2-methyl-propan-1-ol;

1-(3,4-dimethoxyphenyl)-2-[4-[5-[4-[2-(3,4-dimethoxyphenyl)-2-hydroxy-1,1-dimethyl-ethoxy]phenyl]-1,2,4-thiadiazol-3-yl]phenoxy]-2-methyl-propan-1-ol;

1-(3,4-dimethoxyphenyl)-2-[4-[2-[4-[2-(3,4-dimethoxyphenyl)-2-hydroxy-1-methyl-ethoxy]phenyl]oxazol-5-yl]
phenoxy]propan-1-ol;

1-(3,4-dimethoxyphenyl)-2-[4-[2-[4-[2-(3,4-dimethoxyphenyl)-2-hydroxy-ethoxy]phenyl]-1H-imidazol-4-yl]phenoxy]ethanol;

1-(3,4-dimethoxyphenyl)-2-[4-[2-[4-[2-(3,4-dimethoxyphenyl)-2-hydroxy-1,1-dimethyl-ethoxy]phenyl]-1H-imidazol-4-yl]phenoxy]-2-methyl-propan-1-ol;

1-(3,4-dimethoxyphenyl)-2-[4-[2-[4-[2-(3,4-dimethoxyphenyl)-2-hydroxy-1,1-dimethyl-ethoxy]phenyl]-1-methyl-imidazol-4-yl]phenoxy]-2-methyl-propan-1-ol;

1-(3,4-dimethoxyphenyl)-2-[4-[2-[4-[2-(3,4-dimethoxyphenyl)-2-hydroxy-ethoxy]phenyl]-1-methyl-imidazol-4-yl]
phenoxy]ethanol;

1-(3,4-dimethoxyphenyl)-2-[4-[2-[4-[2-(3,4-dimethoxyphenyl)-2-hydroxy-1,1-dimethyl-ethoxy]phenyl]-1-(2-morpholinoethyl)imidazol-4-yl]phenoxy]-2-methyl-propan-1-ol;

1-(3,4-dimethoxyphenyl)-2-[4-[2-[4-[2-(3,4-dimethoxyphenyl)-2-hydroxy-ethoxy]phenyl]-1-(2-morpholinoethyl)
imidazol-4-yl]phenoxy]ethanol hydrochloride;

1-(3,4-dimethoxyphenyl)-2-[4-[2-[4-[2-(3,4-dimethoxyphenyl)-2-hydroxy-ethoxy]phenyl]-4-methyl-oxazol-5-yl]
phenoxy]ethanol;

1-(3,4-dimethoxyphenyl)-2-[4-[5-[4-[2-(3,4-dimethoxyphenyl)-2-hydroxy-ethoxy]phenyl]-1,2,4-oxadiazol-3-yl]
phenoxy]ethanol;

1-[3-(difluoromethoxy)-4-methoxy-phenyl]-2-[4-[2-[4-[2-[3-(difluoromethoxy)-4-methoxy-phenyl]-2-hydroxy-ethoxy]phenyl]thiazol-4-yl]phenoxy]ethanol; and 1-[4-(difluoromethoxy)-3-methoxy-phenyl]-2-[4-[2-[4-[2-[4-(difluoromethoxy)-3-methoxy-phenyl]-2-hydroxy-ethoxy]phenyl]thiazol-4-yl]phenoxy]ethanol.

In accordance with the invention the compounds of general formula (I) can be prepared by the following processes, depending on the nature of the substituent A.

In the text below, a protective group Pg is a group which makes it possible on the one hand to protect a reactive function such as a hydroxyl or an amine during a synthesis and on the other hand allows the reactive function to be restored intact at the end of synthesis. Examples of protective groups and also of methods of protection and deprotection are given in "Protective Groups in Organic Synthesis", Greene et al., 4° Edition (John Wiley & Sons, Inc., New York).

Scheme 1 Suitable for Compounds Having a Substituent A Different from Imidazole and for which R1=R1', R2=R2', R3=R3', R4=R4' and R5=R5'

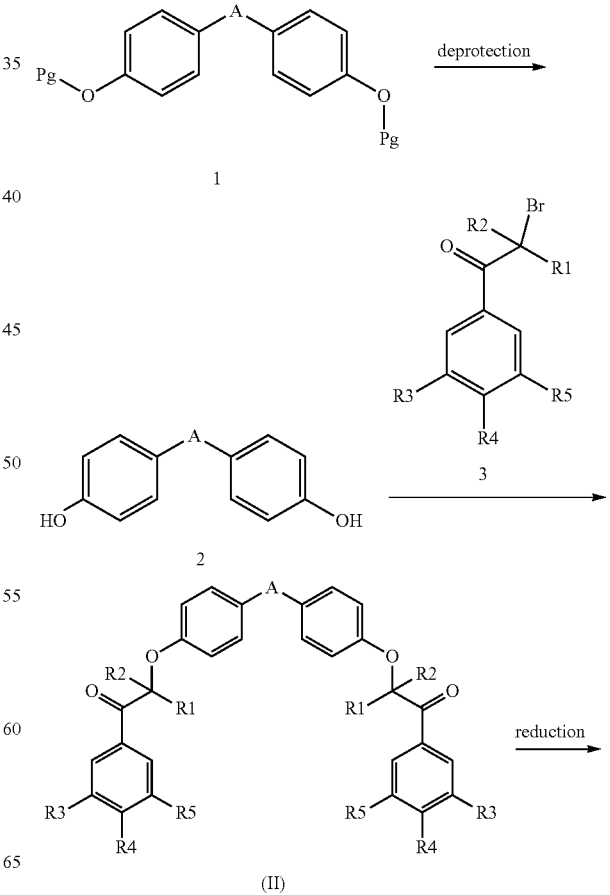

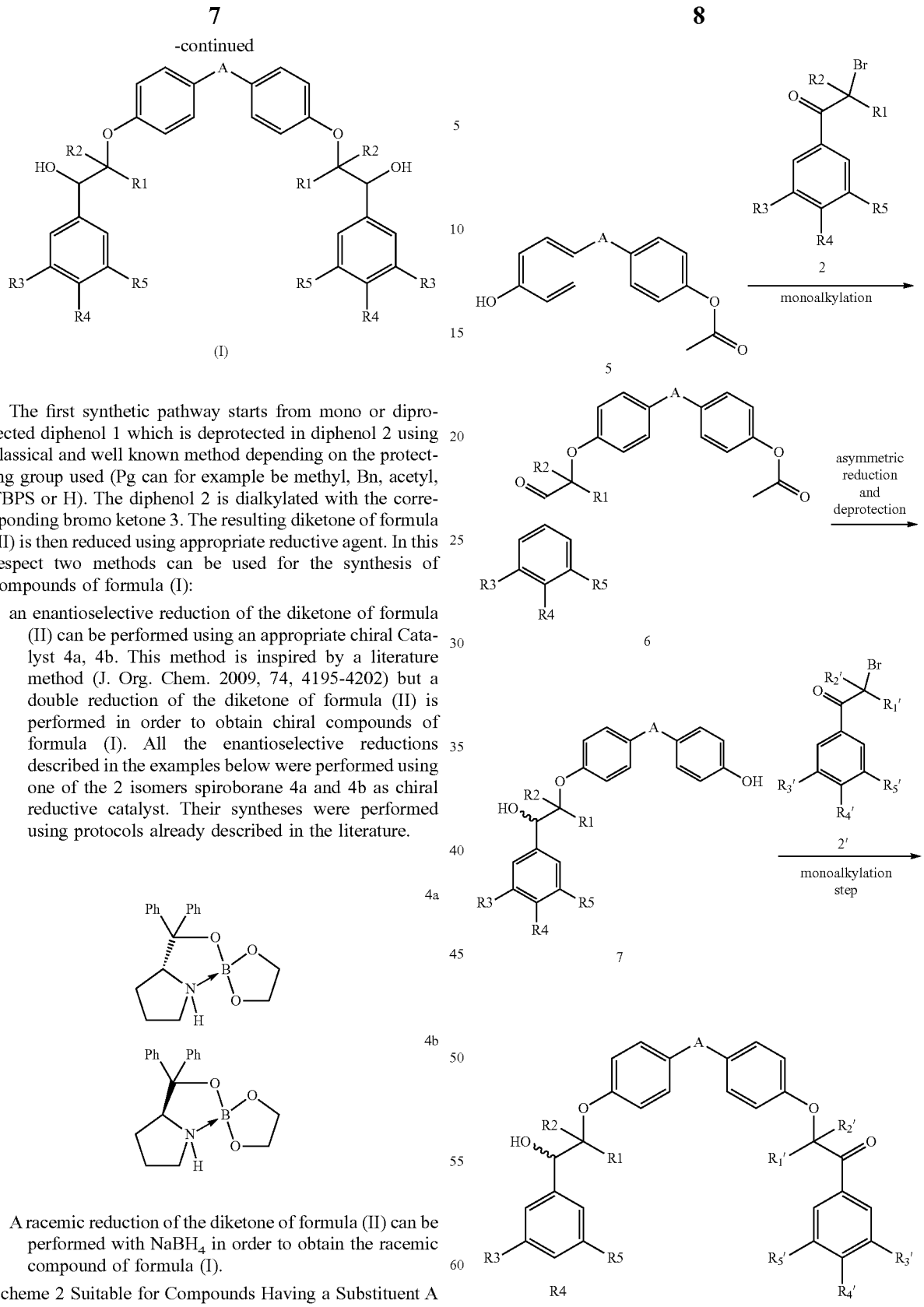

The first synthetic pathway starts from mono or diprotected diphenol 1 which is deprotected in diphenol 2 using classical and well known method depending on the protecting group used (Pg can for example be methyl, Bn, acetyl, TBPS or H). The diphenol 2 is dialkylated with the corresponding bromo ketone 3. The resulting diketone of formula (II) is then reduced using appropriate reductive agent. In this respect two methods can be used for the synthesis of compounds of formula (I):

an enantioselective reduction of the diketone of formula (II) can be performed using an appropriate chiral Catalyst 4a, 4b. This method is inspired by a literature method (J. Org. Chem. 2009, 74, 4195-4202) but a double reduction of the diketone of formula (II) is performed in order to obtain chiral compounds of formula (I). All the enantioselective reductions described in the examples below were performed using one of the 2 isomers spiroborane 4a and 4b as chiral reductive catalyst. Their syntheses were performed using protocols already described in the literature.

A racemic reduction of the diketone of formula (II) can be performed with $NaBH_4$ in order to obtain the racemic compound of formula (I).

Scheme 2 Suitable for Compounds Having a Substituent A Different from Imidazole

In order to be able to obtain derivatives with different substitutions on each side of the molecule, we have identified two different routes which allow a sequential substitution of the phenol and creation of the asymmetric carbons.

-continued

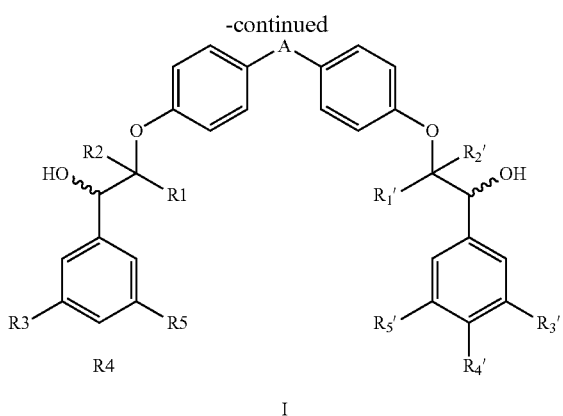

I

Starting from the mono acetate protected phenol 5, the first step of scheme 2 is an alkylation under basic conditions (ex: K₂CO₃) with the corresponding bromoketone 2. This ketone 6 is then subjected to an assymetric reduction step with the reductive agent previously described (4a or 4b of scheme 1) and deprotected also in the same step. The resulting phenol 7 is then alkylated under basic conditions (ex: K₂CO₃) with the corresponding bromoketone 2' which leads to a compound of formula (III) and another reduction step, identical to the last reduction step described in scheme 1 is then performed in order to get final compound of formula (I).

Scheme 3 Suitable for Compounds Having an Imidazol A Substituent

Compounds for which A=2,4-diarylimidazol are prepared with a specific pathway to take into account the reactivity of the imidazole ring.

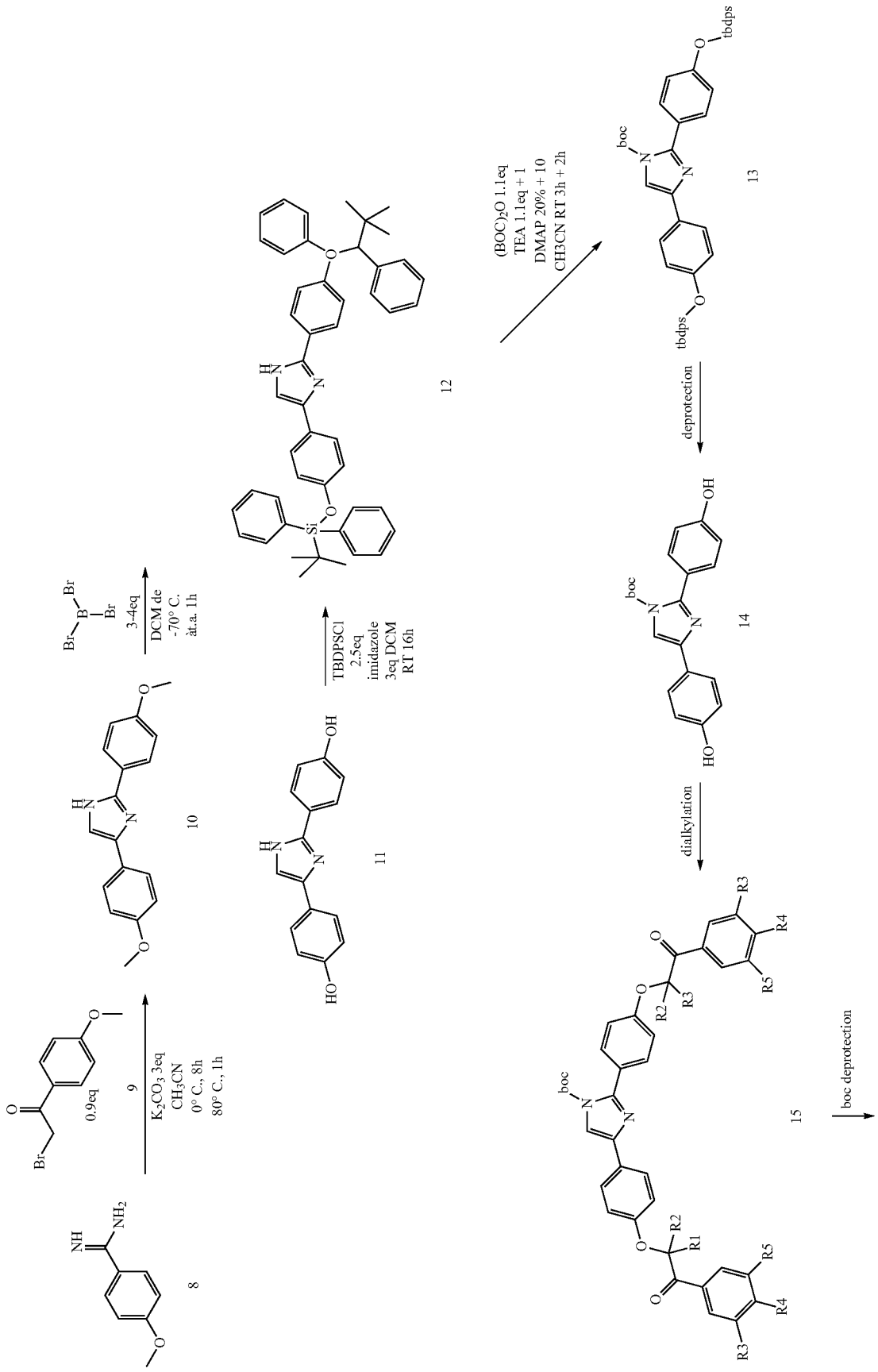

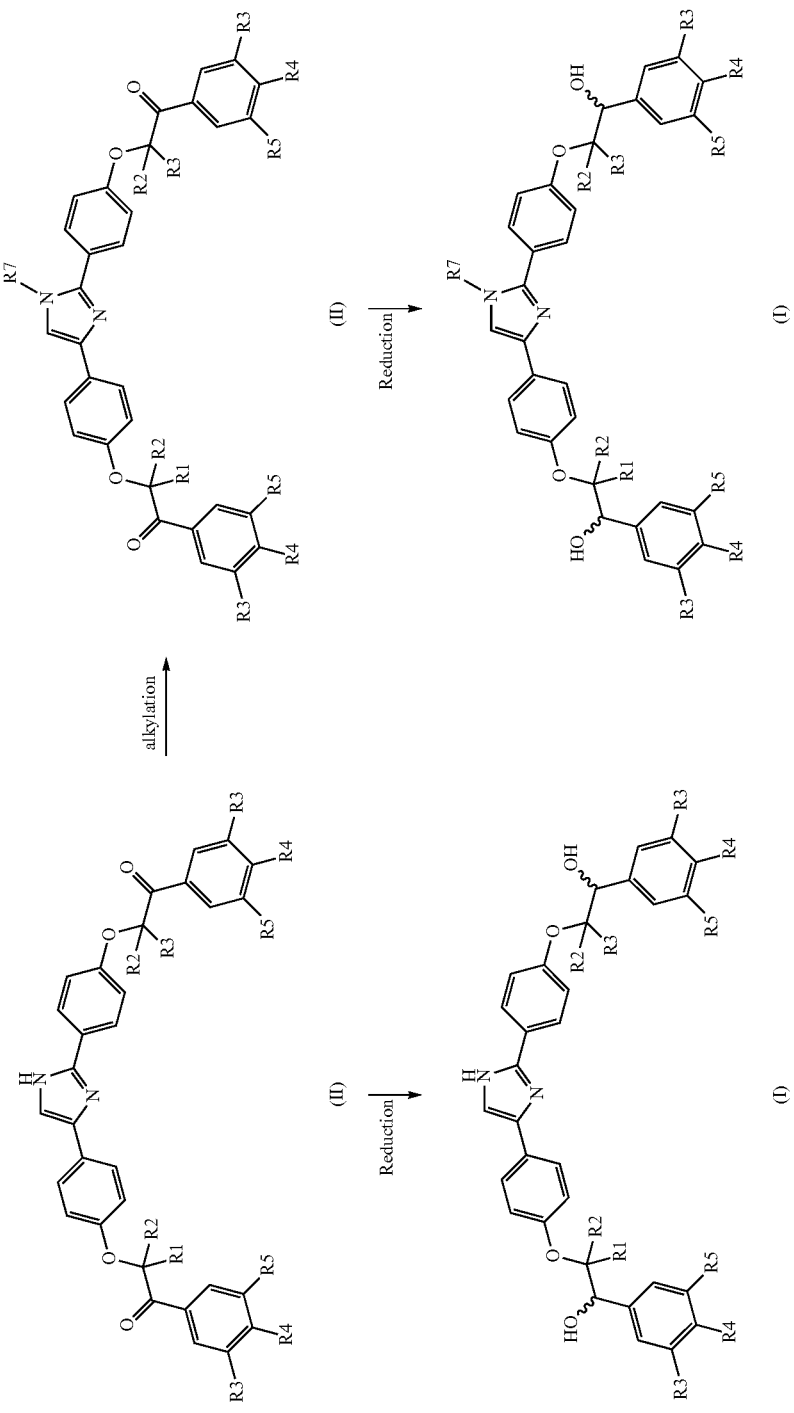

The commercially available amidine 8 is cyclized under basic conditions (K₂CO₃) with the commercially available bromoketone 9 in order to obtain compound 10. The deprotection of compound 10 in the diphenol 11 is performed using BBr₃ conditions. The diphenol 11 is then protected with a silyl protective group (compound 12) and the imidazol ring is protected with Boc group (compound 13). Deprotection of the sylil group and alkylation of the diphenol 14 gives the diketone of formula (II) which can be reduced in the compound of formula (I) or alkylated and then reduced using conditions identical to the last reduction step described in scheme 1 is then performed in order to get final compound of formula (I)

SYNTHESIS OF HETEROCYCLE DIPHENOL COMPOUNDS 2,4-DIARYLOXAZOL AND 2,4-DIARYLTHIAZOL RING SYNTHESIS

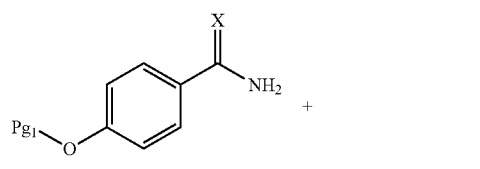

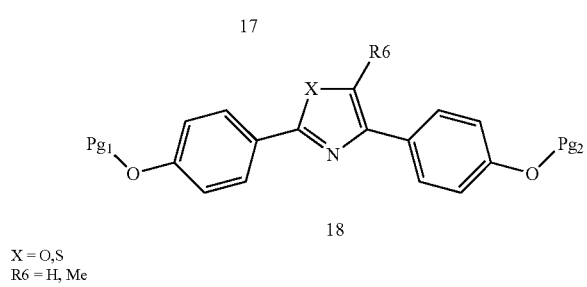

X = O, S
R6 = H, Me

The commercially available substituted amide or thioamine 16 is reacted with the bromoketone 17 in appropriate conditions in order to cyclize in oxazole or thiazole derivatives 18 and those compounds can be directly used as starting material of the general synthesis of the final compounds of formula (I).

2,4-DIARYLTHIOPHEN RING SYNTHESIS

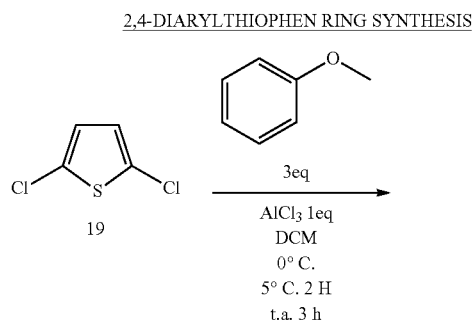

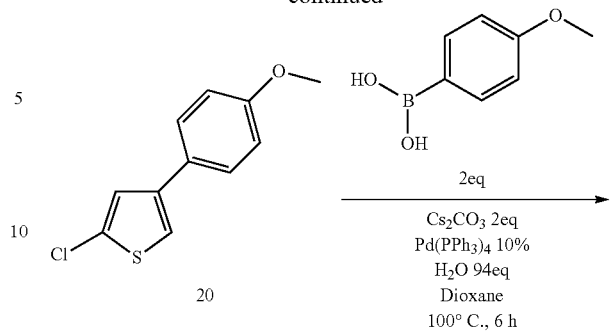

Commercially available dichlorothiophen 19 is reacted with methoxyphenyl in presence of AlCl₃ and gives the 4-aryl thiophen 20 which is reacted with boronic acid in a Suzuki reaction to obtain the 2,4-diarylthiophene 21. This compound can be directly used as starting material in scheme 1.

3,5-DIARYLOXADIAZOL RING SYNTHESIS

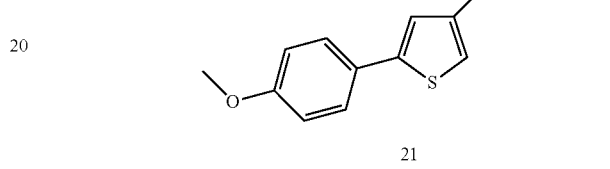

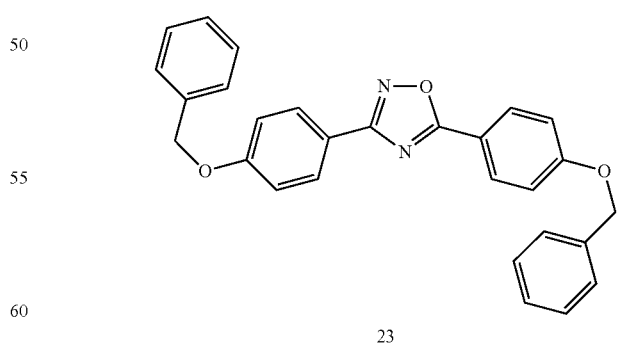

Oxadiazol compound 23 is prepared using a dimerization reaction of the cyano derivate 22 in presence of hydroxylamine and this compound can be directly used as starting material in scheme 1.

2,5-DIARYLOXAZOL RING SYNTHESIS

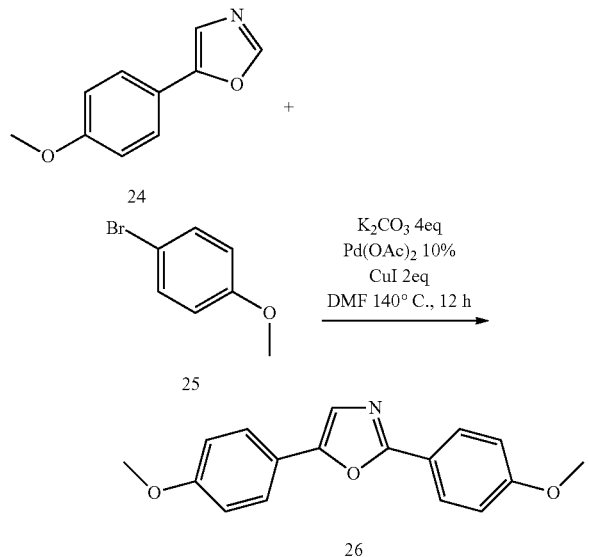

Compound 26 is obtained with a palladium coupling reaction of compound 24 with the bromo anisole 25 in presence of CuI and this compound can be directly used as starting material in scheme 1.

In schemes 1-3, the starting compounds and the reactants, when the way in which they are prepared is not described, are available commercially or are described in the literature, or else may be prepared by methods which are described therein or which are known to a person skilled in the art.

In another of its aspects the invention also provides the compounds of formulae (II) and (III). These compounds are useful as synthesis intermediates for the compounds of formula (I).

EXAMPLES

The examples which follow describe the preparation of certain compounds in accordance with the invention. These examples are not limitative, and merely illustrate the present invention. The numbers of the compounds exemplified match those given in the table hereinafter, which illustrates the chemical structures and physical properties of some compounds according to the invention.

The following abbreviations and empirical formulae are used:

| | |
|---|---|
| AcOEt | ethyl acetate |
| Boc | tert-butyloxycarbonyl |
| CuI | copper iodide |
| DCM | dichloromethane |
| DMAP | 4-dimethylaminopyridine |
| DMF | N,N-dimethylformamide |
| DMSO | dimethyl sulfoxide |
| EtSNa | sodium ethyl sulfide |
| EtOH | ethanol |
| HCl | hydrogen chloride |
| HPLC | high-performance liquid chromatography |
| LCMS | liquid chromatography/mass spectrometry |
| MeOH | methanol |
| NaCl | sodium chloride |
| NaBH$_4$ | sodium borohydride |
| Na$_2$SO$_4$ | sodium sulfate |
| TBDPSiCl | tert-butyldiphenylsilyl chloride |
| TBPS | tris(biphenyl-4-yl)silyl |
| TFA | trifluoroacetic acid |
| THF | tetrahydrofuran |
| THP | tetrahydropyranyl |
| ° C. | degrees Celsius |
| RT | room temperature |
| Rt | retention time |
| min | minute(s) |
| mL | millilitre(s) |
| mmol | millimole(s) |
| ppm | parts per million |

The chiral HPLC method able to separate the compounds was identified using a mixture of isomers obtained according to the racemic reduction described in scheme 1 and was then used to determine the chiral UV purity of all described compounds.

In the examples described herein below the following analytical methods were used: The proton nuclear magnetic resonance spectra (1H NMR) were recorded on Bruker spectrometers (250, 400 and 500 MHz) in DMSO-d6 or DCCl$_3$. The chemical shifts δ were expressed in parts per million (ppm). The following abbreviations were used for interpreting the spectra: s: singlet, d: doublet, t: triplet, q: quadruplet, quint: quintuplet, sext: sextuplet, m: multiplet, dd: doublet of doublets, br: broad peak.

The different LCUVMS methods which were used are detailed below.

Method 1:
UPLC 220 nm
Column Acquity UPLC BEH C18 (2.1×50 mm) 1.7 μm
Eluent A=H2O+0.02% HCOOH.
Eluent B=CH3CN+0.02% HCOOH.
T° C.: 55° C.
Gradient: t0 2% de B, t4 min 98% de B, t4.5 min 98% de B, t4.6 min 2% de B, t5.0. min 2% de B.
Flow rate=1 ml/min Method 2:
HPLC 1100 polar mode UV=220 nM, column DAICEL Chiralpak IB (250 mm×4.6) 5 μm, 100% methanol, flowrate 1 mL/min, T=25° C., injection 10 μL at 0.5 mg/mL of MeOH Method 3:
HPLC 1100 polar mode UV=210 nM, column DAICEL Chiralpak IC (250 mm×4.6) 5 μm, 100% acetonitrile, flowrate 1 mL/min, T=25° C., injection 10 μL at 0.5 mg/mL of MeOH Method 4:
HPLC Agilent 1100 UV=210 nM, column DAICEL Chiralpak OD-H (100 mm×4.6) 5 μm, 100% MeOH, flowrate 0.8 mL/min, T=25° C., injection 2 μL at 0.5 mg/mL of MeOH Method 5:
Instrument: Waters HPLC: Alliance 2695, UV: PDA 996, MS: ZQ (simple Quad) ZQ2
Software: Masslynx, OpenLynx
LC Conditions:
Column: Luna C18 (2)-HST Phenomenex (30×2 mm) 2.5 μm
Column temperature: 50° C.
Eluent A: H$_2$O+0.05% TFA (v/v)
Eluent B: CH3CN+0.035% TFA (v/v)
Gradient: t0 0% de B, t2.5 min 100% de B, t3.5 min 100% de B, t3.6 min 0% de B, t5 min 0% de B
Flow rate: 1 ml/min
Split: ⅓ to the MS source
Injection: 2 μl
UV detection: extraction 220 nm MS Conditions:
Ionization mode: positive electrospray ES+
Capillary tension: 3.5 kV
Cone Tension: 30V
Desolvation Temperature: 300° C.
Source Temp.: 130° C.
Method 6:
Instrument: Waters UPLC: Acquity, UV: Acquity PDA, MS: SQD (simple Quad) SQW
Software: Masslynx, OpenLynx
LC Conditions:
Column: BEH C18 Waters (50×2.1 mm) 1.7 μm
Temp. Column: 55° C.
Eluent A: H$_2$O+0.05% TFA (v/v)
Eluent B: CH3CN+0.035% TFA (v/v)
Gradient: t0 2% de B, t2.4 min 98% de B, t3.0 min 98% de B, t3.03 min 2% de B, t3.5 min 2% de B
Flow rate: 0.8 ml/min
Injection: 0.3 μl
UV Detection: extraction 220 nm
MS conditions:
Ionization mode: positive electrospray ES+
Capillary tension: 3 kV
Cone tension: 30V
Desolvation Temperature: 500° C.
Source Temp.: 150° C.

Examples Prepared According to Scheme 1

Example 1: Synthesis of 2,4-Bis-(4-hydroxyphenyl)-thiazole 2,4-Bis-(4-methoxyphenyl)-thiazole 1 (1 eq, 5 g, 16.81 mmol) was dissolved in 50 mL of DMF then EtSNa (6 eq, 8.49 g, 100.88 mmol) was added and stirring at RT. The reaction mixture was warmed to 120° C. for 12 h, and then cooled to RT. 200 mL of AcOEt were added and the suspension obtained was filtered. The solid was stirred with 200 mL of AcOEt and 200 mL of 1M solution of HCl for 16 h at RT then the suspension was filtered and the solid was dried under reduced pressure to give 3.5 g (77% yield) of 2,4-Bis-(4-hydroxyphenyl)-thiazole.

1H NMR (400 MHz, DMSO-d6) δ ppm 9.20 (br. s, 2H) 7.84 (d, J=1.8 Hz, 2H) 7.82 (d, J=1.8 Hz, 2H) 7.76 (s, 1H) 6.89 (d, J=8.7 Hz, 2H) 6.84 (d, J=8.7 Hz, 2H) LCMS (Method 3): 100% (purity at 210 nM) Rt=5 min

Example 2: Synthesis of 1-(3,4-Dimethoxy-phenyl)-2-[4-(4-{4-[2-(3,4-dimethoxy-phenyl)-2-oxo-ethoxy]-phenyl}-thiazol-2-yl)-phenoxy]-ethanone II-1

The diphenol obtained in example 1 (1 eq, 500 mg, 1.86 mmol) was dissolved in 10 mL of DMF at RT, K$_2$CO$_3$ (6 eq, 1.54 g, 11.16 mmol) was added and 2-Bromo-1-(3,4-dimethoxy-phenyl)-ethanone (1.16 g, 4.46 mmol). The reaction mixture was stirred at RT 16 h then filtered. The solution was evaporated under reduced pressure. The solid was then dissolved in DCM and washed with saturated solution of Na$_2$CO$_3$ then water. The organic layer was dried over Na$_2$SO$_4$, filtered and concentrated under reduced pressure. The residue was purified by silica gel chromatography (eluent: heptane/AcOEt 1/0 to 1/1) to give, after evaporation, 228 mg of II-1 (20% yield).

1H NMR (400 MHz, CHLOROFORM-d δ ppm 7.97 (d, J=8.3 Hz, 2H) 7.91 (d, J=8.3 Hz, 2H) 7.67 (t, J=6.0 Hz, 2H) 7.58 (br. s, 2H) 7.28 (s, 1H) 7.01 (d, J=8.3 Hz, 4H) 6.93 (d, J=8.3 Hz, 2H) 5.30 (s, 2H) 5.27 (s, 2H) 3.97 (s, 6H) 3.95 (s, 6H)

LCMS (Method 1): 91.4% (purity at 220 nM) Rt=2.64 min m/z=626.1

Example 3: Synthesis of 1-(3,4-Dimethoxy-phenyl)-2-[4-(4-{4-[2-(3,4-dimethoxy-phenyl)-2-hydroxy-ethoxy]-phenyl}-thiazol-2-yl)-phenoxy]-ethanol (isomer 2) compound I-23

The borane catalyst 4a (33.3 mg, 0.1 mmol) was dissolved in 1 mL of THF then 0.34 ml (0.69 mmol) of 2 M solution of BH$_3$/Me$_2$S was added dropwise and the reaction mixture was stirred 1 h at RT. A suspension of the diketone II-1 obtained in example 2 (0.215 g, 0.34 mmol) in 1.5 mL of THF was added at −20° C. under nitrogen. The reaction was allowed to warm to RT and stirred at this temperature for 20 h. 5 mL of methanol were added and the mixture was concentrated under vacuum. 20 mL of AcOEt was added and the mixture was washed with 1M solution of HCl in water (2×20 ml), 30 mL of water and 30 mL of NaCl (saturated solution) and then dried over Na$_2$SO$_4$, filtered and concentrated under reduced pressure. The residue was purified by silica gel chromatography (eluent: AcOEt/cyclohexane 15/85 to 1/1) to afford, after evaporation, 1-(3,4-Dimethoxy-phenyl)-2-[4-(4-{4-[2-(3,4-dimethoxy-phenyl)-2-hydroxy-ethoxy]-phenyl}-thiazol-2-yl)-phenoxy]-ethanol (compound I-23).

Yield: 301 mg, 75%

1H NMR (400 MHz, DMSO-d6) δ ppm 7.94 (d, J=6.7 Hz, 2H) 7.92 (d, J=6.7 Hz, 2H) 7.90 (s, 1H) 7.05-7.10 (m, 4H) 7.02 (d, J=8.8 Hz, 2H) 6.98 (dd, J=8.3, 1.4 Hz, 2H) 6.93 (d, J=8.3 Hz, 2H) 5.59 (d, J=4.5 Hz, 1H) 5.56 (d, J=4.5 Hz, 1H) 4.89 (quin, J=4.9 Hz, 2H) 4.07 (d, J=5.8 Hz, 2H) 4.04 (d, J=5.8 Hz, 2H) 3.77 (s, 6H) 3.74 (s, 6H)

Chiral chromatography (Method 3): 98.9% (purity at 210 nM) Rt=10.1 min.

Example 4: Synthesis of 1-(3,4-Dimethoxy-phenyl)-2-[4-(4-{4-[2-(3,4-dimethoxy-phenyl)-2-hydroxy-ethoxy]-phenyl}-thiazol-2-yl)-phenoxy]-ethanol (isomer 1) compound I-24

This compound was obtained using the method described in example 3 for compound I-23 but with 4b instead of 4a as chiral catalyst agent 1H NMR (400 MHz, DMSO-d6) δ ppm 7.94 (d, J=6.7 Hz, 2H) 7.92 (d, J=6.7 Hz, 2H) 7.90 (s, 1H) 7.05-7.10 (m, 4H) 7.02 (d, J=8.8 Hz, 2H) 6.98 (dd, J=8.3, 1.4 Hz, 2H) 6.93 (d, J=8.3 Hz, 2H) 5.59 (d, J=4.5 Hz, 1H) 5.56 (d, J=4.5 Hz, 1H) 4.89 (quin, J=4.9 Hz, 2H) 4.07 (d, J=5.8 Hz, 2H) 4.04 (d, J=5.8 Hz, 2H) 3.77 (s, 6H) 3.74 (s, 6H)

Chiral chromatography (Method 3): 81.2% (purity at 210 nM) Rt=13.6 min

Example 5: Synthesis of 1-(3,4-Dimethoxy-phenyl)-2-[4-(4-{4-[2-(3,4-dimethoxy-phenyl)-2-hydroxy-ethoxy]-phenyl}-thiazol-2-yl)-phenoxy]-ethanol (isomer 1, 2, 3 and 4) compound I-69

To a suspension of the diketone II-1 (0.4 mg, 1 eq.) in MeOH 13 mL NaBH$_4$ (0.241 mg, 10 eq.) were added at RT under N$_2$. After 3 days 5 eq. of NaBH$_4$ was added and the reaction mixture stirred 24 h at RT. 10 ml of HCl 1N was then added, the MeOH was evaporated and DCM was added. The organic layer was separated and washed with water. After separation, the organic phase was dried over Na$_2$SO$_4$ filtered and concentrated under reduced pressure. The residue was purified by silica gel chromatography (eluent: AcOEt/cyclohexane 15/85 to 1/1) to afford, after evaporation, 1-(3,4-Dimethoxy-phenyl)-2-[4-(4-{4-[2-(3,4-dimethoxy-phenyl)-2-hydroxy-ethoxy]-phenyl}-thiazol-2-yl)-phenoxy]-ethanol (compound I-69).

Yield: 301 mg, 75%

1H NMR (400 MHz, DMSO-d6) δ ppm 7.92 (5H) 6.91-7.10 (15H) 5.56 (2H) 4.89 (2H) 4.06 (4H) 3.77 (s, 6H) 3.74 (s, 6H)

Chiral chromatography (Method 3):
Isomer 1: 25.8% (purity at 210 nM) Rt=10.3 min.
Isomer 2: 24.5% (purity at 210 nM) Rt=11.5 min.
Isomer 3: 25.1% (purity at 210 nM) Rt=11.8 min.
Isomer 4: 24.6% (purity at 210 nM) Rt=13.6 min.

Examples Prepared According to Scheme 2

Example 6: Synthesis of acetic acid 4-[2-(4-hydroxy-phenyl)-thiazol-4-yl]-phenyl ester 1.66 g of 4-hydroxythiobenzamide (1 eq, 6.46 mmol) and 0.99 g of Acetic acid 4-(2-bromo-acetyl)-phenyl ester (1 eq, 6.46 mmol) were dissolved in 25 mL of CH$_3$CN and heated at reflux for 1 h. After cooled down to RT over a 2 h period the solid formed was filtered off, washed with a minimum of EtOH and dried under vacuum at 40° C. overnight. 1.99 g of acetic acid 4-[2-(4-hydroxy-phenyl)-thiazol-4-yl]-phenyl ester were obtained (99% yield).

1H NMR (400 MHz, DMSO-d6) δ ppm 10.29 (br. s, 1H) 8.06 (d, J=8.7 Hz, 2H) 8.03 (s, 1H) 7.86 (d, J=8.7 Hz, 2H) 7.23 (d, J=8.7 Hz, 2H) 6.90 (d, J=8.7 Hz, 2H) 2.30 (s, 3H)

LCUV-MS: 99% (purity at 220 nM) Rt=2.24 min m/z=312 (method 5)

Example 7: Synthesis of acetic acid 4-(2-{4-[2-(3,4-dimethoxy-phenyl)-2-oxo-ethoxy]-phenyl}-thiazol-4-yl)-phenyl ester The phenol obtained in example 6 (1 eq, 1 g, 3.21 mmol) was dissolved in 16 mL of DMF at RT, K$_2$CO$_3$ (4 eq, 1.77 g, 12.85 mmol) was added and 2-Bromo-1-(3,4-dimethoxy-phenyl)-ethanone (1.5 eq, 1.25 g, 4.82 mmol). The reaction mixture was stirred at RT 16 h then filtered. The solution was evaporated under reduced pressure. The solid was then dissolved in DCM and washed with saturated solution of Na$_2$CO$_3$ then water. The organic layer was dried over Na$_2$SO$_4$, filtered and concentrated under reduced pressure. The residue was purified by silica gel chromatography (eluent: DCM/AcOEt 1/0 to 96/4) to give, after evaporation, 736 mg of acetic acid 4-(2-{4-[2-(3,4-dimethoxy-phenyl)-2-oxo-ethoxy]-phenyl}-thiazol-4-yl)-phenyl ester (47% yield).

1H NMR (600 MHz, DMSO-d6) δ ppm 8.09 (s, 1H) 8.08 (d, J=8.7 Hz, 2H) 7.97 (d, J=8.8 Hz, 2H) 7.76 (dd, J=8.5, 2.1 Hz, 1H) 7.53 (d, J=2.1 Hz, 1H) 7.25 (d, J=8.7 Hz, 2H) 7.15 (d, J=8.5 Hz, 1H) 7.12 (d, J=8.8 Hz, 2H) 5.65 (s, 2H) 3.89 (s, 3H) 3.86 (s, 3H) 2.31 (s, 3H)

LCUV-MS: 99% (purity at 220 nm) Rt=2.56 min m/z=489.9 (method 5)

Example 8: Synthesis of 4-(2-{4-[2-(3,4-Dimethoxy-phenyl)-2-hydroxy-ethoxy]-phenyl}-thiazol-4-yl)-phenol (isomer 2)

1.86 mL of BH$_3$-Me$_2$S 2M in THF (4 eq, 3.72 mmol) and 150.2 mg of boronate 4a (0.5 eq, 0.464 mmol) were stirred together at RT under N$_2$ for 30 min. The mixture was cooled to 0° C. then the ketone obtained in example 7 (1 eq, 455 mg, 0.929 mmol) in THF suspension was slowly added. The reaction was stirred 72 h at RT. The reaction mixture was poured onto 20 mL of MeOH and the mixture evaporated to dryness. 30 mL of DCM was added and this organic layer washed with HCl 1N (20 mL). Aqueous layer was separated and extracted 2 times with 10 mL of DCM. Organic layers were combined, dried with Na$_2$SO$_4$ and evaporated. The residue was purified by silica gel chromatography (eluent: DCM/MeOH 1/0 to 97/3) to afford, after evaporation, 362.8 mg (87% yield) of 4-(2-{4-[2-(3,4-Dimethoxy-phenyl)-2-hydroxy-ethoxy]-phenyl}-thiazol-4-yl)-phenol.

1H NMR (400 MHz, DMSO-d6) δ ppm 9.61 (s, 1H) 7.92 (d, J=8.8 Hz, 2H) 7.84 (d, J=8.7 Hz, 2H) 7.80 (s, 1H) 7.07 (d, J=8.8 Hz, 2H) 7.07 (d, J=1.8 Hz, 1H) 6.98 (dd, J=8.3, 1.8 Hz, 1H) 6.93 (d, J=8.3 Hz, 1H) 6.84 (d, J=8.7 Hz, 2H) 5.59 (d, J=4.7 Hz, 1H) 4.90 (q, J=5.4 Hz, 1H) 4.07 (d, J=5.8 Hz, 2H) 3.77 (s, 3H) 3.75 (s, 3H)

Chiral chromatography (Method 4): 93.5% (purity at 210 nM) Rt=3.9 min.

Example 9: Synthesis of 1-(3,4-Dimethoxy-phenyl)-2-[4-(2-{4-[2-(3,4-dimethoxy-phenyl)-2-hydroxy-ethoxy]-phenyl}-thiazol-4-yl)-phenoxy]-ethanone (isomer 2)

The phenol obtained in example 8 (1 eq, 360 mg, 0.8 mmol) was dissolved in 10 mL of DMF at RT, K$_2$CO$_3$ (4 eq, 442.7 mg, 3.2 mmol) was added and 2-Bromo-1-(3,4-dimethoxy-phenyl)-ethanone (1.5 eq, 327.6 mg, 1.2 mmol). The reaction mixture was stirred at RT 16 h then filtered. The solution was evaporated under reduced pressure. The solid was then dissolved in DCM and washed with saturated solution of Na$_2$CO$_3$ then water. The organic layer was dried over Na$_2$SO$_4$, filtered and concentrated under reduced pressure to give, after evaporation, 500 mg of 1-(3,4-Dimethoxy-phenyl)-2-[4-(2-{4-[2-(3,4-dimethoxy-phenyl)-2-hydroxy-ethoxy]-phenyl}-thiazol-4-yl)-phenoxy]-ethanone (compound of formula (III), 99% yield).

1H NMR (400 MHz, DMSO-d6) δ ppm 7.89-7.98 (m, 5H) 7.75 (dd, J=8.5, 1.9 Hz, 1H) 7.51 (d, J=1.9 Hz, 1H) 7.13 (d, J=8.5 Hz, 1H) 7.06 (dd, J=13.1, 8.7 Hz, 5H) 6.98 (dd, J=8.2, 1.7 Hz, 1H) 6.93 (d, J=8.2 Hz, 1H) 5.56-5.60 (m, 3H) 4.90 (q, J=5.4 Hz, 1H) 4.07 (d, J=5.8 Hz, 2H) 3.87 (s, 3H) 3.84 (s, 3H) 3.77 (s, 3H) 3.75 (s, 3H)

LCUV-MS: 88% (purity at 220 nm) Rt=2.59 min m/z=628 (method 5)

Chiral chromatography (method 3): 94% (purity at 210 nm) Rt=8.9 min.

Example 10: Synthesis of 1-(3,4-Dimethoxy-phenyl)-2-[4-(4-{4-[2-(3,4-dimethoxy-phenyl)-2-hydroxy-ethoxy]-phenyl}-thiazol-2-yl)-phenoxy]-ethanol (isomer 3) compound I-61

This compound was obtained using the general method of asymmetric reduction previously described. 60% yield.

0.478 mL of BH$_3$-Me$_2$S 2M in THF (6 eq, 0.956 mmol) and 46.34 mg of boronate 4a (0.9 eq, 0.143 mmol) were stirred together at RT under N$_2$ for 15 min. The mixture was cooled to −20° C. then a solution of the ketone of formula (III) obtained in example 9 (1 eq, 100 mg, 0.159 mmol) in THF was slowly added. The reaction was stirred 16 h at RT. The reaction mixture was poured onto 15 mL of MeOH and the mixture evaporated to dryness. 30 mL of DCM was added and this organic layer washed with HCl 1N (20 mL).

Aqueous layer was separated and extracted 2 times with 10 mL of DCM. Organic layers were combined, dried with Na$_2$SO$_4$ and evaporated. The residue was purified by silica gel chromatography (eluent: DCM/MeOH 1/0 to 97/3) to afford, after evaporation, 59.9 mg (60% yield) of 1-(3,4-Dimethoxy-phenyl)-2-[4-(4-{4-[2-(3,4-dimethoxy-phenyl)-2-hydroxy-ethoxy]-phenyl}-thiazol-2-yl)-phenoxy]-ethanol (compound I-61).

1H NMR (400 MHz, DMSO-d6)/ppm 7.94 (d, J=6.7 Hz, 2H) 7.92 (d, J=6.7 Hz, 2H) 7.90 (s, 1H) 7.05-7.11 (m, 4H) 7.02 (d, J=8.8 Hz, 2H) 6.98 (dd, J=8.3, 1.0 Hz, 2H) 6.93 (d, J=8.3 Hz, 2H) 5.59 (d, J=4.7 Hz, 1H) 5.56 (d, J=4.7 Hz, 1H) 4.89 (quin, J=5.0 Hz, 2H) 4.07 (d, J=5.8 Hz, 2H) 4.04 (d, J=5.8 Hz, 2H) 3.77 (s, 6H) 3.75 (s, 6H)

LCUV-MS: 98% (purity at 220 nm) Rt=2.39 min m/z=630 (method 1)

Chiral chromatography (method 2): 88.2% (purity at 210 nm) Rt=22.7 min.

Example 11: Synthesis of 1-(3,4-Dimethoxy-phenyl)-2-[4-(4-{4-[2-(3,4-dimethoxy-phenyl)-2-hydroxy-ethoxy]-phenyl}-thiazol-2-yl)-phenoxy]-ethanol (isomer 3) I-62

Same procedure (second synthetic route: scheme 2) was performed as in example 10 but the enantioselective reduction were performed with boronate 4b instead of 4a in order to obtained the other enantiomer (isomer 3) compound I-62

1H NMR (400 MHz, DMSO-d6) δ ppm 7.94 (d, J=6.7 Hz, 2H) 7.92 (d, J=6.7 Hz, 2H) 7.90 (s, 1H) 7.05-7.11 (m, 4H) 7.02 (d, J=8.8 Hz, 2H) 6.98 (dd, J=8.3, 1.0 Hz, 2H) 6.93 (d, J=8.3 Hz, 2H) 5.59 (d, J=4.7 Hz, 1H) 5.56 (d, J=4.7 Hz, 1H) 4.89 (quin, J=5.0 Hz, 2H) 4.07 (d, J=5.8 Hz, 2H) 4.04 (d, J=5.8 Hz, 2H) 3.77 (s, 6H) 3.75 (s, 6H)

LCUV-MS: 99.4% (purity at 220 nm) RT=2.39 min m/z=630 (method 1)

Chiral chromatography (method 2): 81.5% (purity at 220 nm) Rt=21 min.

Examples Prepared According to Scheme 3

Example 12: Synthesis of 2,4-Bis-(4-methoxy-phenyl)-1H-imidazole 10

To a suspension of the commercially available 4-methoxythiobenzamide 8 (1 eq, 9.1 g, 60.59 mmol) in 200 mL of acetonitrile was added 25 g of K$_2$CO$_3$ (3 eq, 181.78 mmol) and at 0° C. 12.49 g of bromo-1-(4-methoxyphenyl)-ethanone 9 (0.9 eq, 54.53 mmol). The mixture was stirred at 0° C. for 8 h then warmed to room temperature overnight. The reaction mixture was warmed to 80° C. for 1 h, cooled to room temperature and filtered. The solid was washed with acetonitrile then triturated with water and filtered to give 12.6 g of 2,4-Bis-(4-methoxy-phenyl)-1H-imidazole (74% yield).

1H NMR (400 MHz, DMSO-d6) δ ppm 12.35 (br. s., 0.7H) 12.22 (br. s, 0.3H) 7.95 (d, J=8.8 Hz, 2H) 7.76 (d, J=8.0 Hz, 1.4H) 7.68 (br. s, 0.6H) 7.56 (s, 0.7H) 7.28 (br. s., 0.3H) 7.03 (d, J=8.8 Hz, 2H) 6.94 (d, J=8.0 Hz, 2H) 3.81 (s, 3H) 3.77 (s, 3H) (2 tautomer's forms 70/30)

LCUV-MS: Rt=1.64 min m/z=281 (method 5)

Example 13: Synthesis of 2,4-Bis-(4-hydroxy-phenyl)-1H-imidazole 11

To a suspension of 2,4-Bis-(4-methoxy-phenyl)-1H-imidazole (1 eq, 1 g, 3.57 mmol) in DCM (90 mL) at −70° C. were slowly added 10.7 mL of BBr$_3$ (3 eq, 10.7 mmol). The solution was warmed to room temperature and stirred 1 h. The mixture was cooled to −70° C. and water was added (100 mL). At room temperature ethyl acetate and a saturated solution of NaHCO$_3$ was added then the isolated organic layer was washed with water and brine then dried with Na$_2$SO$_4$, filtered and concentrated under vacuum pressure. 0.8 g of 2,4-Bis-(4-hydroxy-phenyl)-1H-imidazole was obtained (89% yield).

H NMR (400 MHz, DMSO-d6) δ ppm 12.17 (br. s., 0.7H) 12.07 (br. s., 0.3H) 9.61 (br. s., 0.7H) 9.47 (br. s., 0.3H) 9.26 (br. s., 1H) 7.81-7.85 (m, 0.6H) 7.78 (d, J=8.6 Hz, 1.4H) 7.62 (d, J=8.3 Hz, 1.4H) 7.51-7.58 (m, 0.6H) 7.43 (s, 0.7H) 7.17 (br. s., 0.3H) 6.82 (d, J=8.6 Hz, 2H) 6.75 (d, J=8.3 Hz, 2H) (2 tautomer's forms 70/30)

LCUV-MS: Rt=1.4 min m/z=253 (method 5)

Example 14: Synthesis of 2,4-Bis-[4-(tert-butyl-diphenyl-silanyloxy)-phenyl]-1H-imidazole 12

To a suspension of 2,4-Bis-(4-hydroxy-phenyl)-1H-imidazole (1 eq, 1 g, 3.96 mmol) in DCM were added 0.809 g of imidazole (3 eq, 11.89 mmol) and 2.63 mL of TBDPSiCl (2.5 eq, 9.91 mmol). The mixture was stirred at room temperature for 16 h then filtered. The filtrate was washed with saturated solution of NaHCO$_3$ water and brine then dried with Na$_2$SO$_4$, filtered and concentrated under vacuum pressure. The solid was triturated with MeOH, filtered and the solid was washed with MeOH then dried under vacuum at 50° C. 1.86 g of 2,4-Bis-[4-(tert-butyl-diphenyl-silanyloxy)-phenyl]-1H-imidazole was obtained (64% yield).

1H NMR (400 MHz, DMSO-d6) δ ppm 12.26 (s, 0.7H) 12.11 (s, 0.3H) 7.66-7.72 (m, 10H) 7.56 (d, J=8.6 Hz, 2H) 7.41-7.52 (m, 13H) 6.79 (d, J=8.7 Hz, 2H) 6.72 (d, J=8.6 Hz, 2H) 1.06 (s, 9H) 1.06 (s, 9H) (2 tautomer's forms 70/30)

LCUV-MS: Rt=2.91 min m/z=729 (method 5)

Example 15: Synthesis of 2,4-Bis-[4-(tert-butyl-diphenyl-silanyloxy)-phenyl]-imidazole-1-carboxylic acid tert-butyl ester 13

To a suspension of 2,4-Bis-[4-(tert-butyl-diphenyl-silanyloxy)-phenyl]-1H-imidazole (1 eq, 1.3 g, 1.82 mmol) in 25 mL of acetonitrile was added at room temperature triethylamine (1.1 eq, 280 µL, 2 mmol), (Boc)$_2$O (2 eq, 0.82 g, 3.64 mmol) and DMAP (0.2 eq, 44.5 mg, 0.36 mmol). The mixture was stirred 4 h then filtered and the solid was washed with acetonitrile. The solid was dried under vacuum at 50° C. 2,4-Bis-[4-(tert-butyl-diphenyl-silanyloxy)-phenyl]-imidazole-1-carboxylic acid tert-butyl ester was obtained in 41% yield.

1H NMR (400 MHz, DMSO-d6) δ ppm 7.88 (s, 1H) 7.65-7.73 (m, 8H) 7.61 (d, J=8.6 Hz, 2H) 7.40-7.53 (m, 12H) 7.34 (d, J=8.6 Hz, 2H) 6.78 (d, J=8.7 Hz, 2H) 6.74 (d, J=8.7 Hz, 2H) 1.30 (s, 9H) 1.06 (s, 9H) 1.05 (s, 9H)

LCUV-MS: Rt=2.66 min m/z=829 (method 6)

Example 16: Synthesis of 2,4-Bis-(4-hydroxy-phenyl)-imidazole-1-carboxylic acid tert-butyl ester 14

2,4-Bis-[4-(tert-butyl-diphenyl-silanyloxy)-phenyl]-imidazole-1-carboxylic acid tert-butyl ester obtained in example 15 (1 eq, 1.09 g, 1.31 mmol) was dissolved in 20 mL of THF at 0° C., 2.63 mL of TBAF (2 eq, 2.63 mmol) was then added and the reaction mixture was stirred at 0° C. 4 h. Ethyl acetate and a saturated solution of NaHCO$_3$ was added, then isolated organic layer was washed with water and brine then dried with Na$_2$SO$_4$, filtered and concentrated under vacuum pressure. The residue was purified by silica gel chromatography (eluent: CH$_2$Cl$_2$/MeOH 98/2 to 90/10) to afford, after evaporation, 72% yield.

1H NMR (400 MHz, DMSO-d6) δ ppm 9.73 (br. s., 1H) 9.47 (br. s., 1H) 7.85 (s, 1H) 7.68 (d, J=8.7 Hz, 2H) 7.40 (d, J=8.6 Hz, 2H) 6.82 (d, J=8.7 Hz, 2H) 6.78 (d, J=8.6 Hz, 2H) 1.41 (s, 9H)

LCUV-MS: Rt=1.85 min m/z=353 (method 5)

Example 17: Synthesis of 2,4-Bis-{4-[2-(3,4-dimethoxy-phenyl)-2-oxo-ethoxy]-phenyl}-imidazole-1-carboxylic acid tert-butyl 15

The diphenol obtained in example 16 (1 eq, 450 mg, 1.28 mmol) was dissolved in 10 mL of DMF at RT, K$_2$CO$_3$ (6 eq, 1.06 g, 7.66 mmol) was added and 2-Bromo-1-(3,4-dimethoxy-phenyl)-ethanone (4 eq, 1.32 g, 5.11 mmol). The reaction mixture was stirred at RT 16 h then filtered. The solution was evaporated under reduced pressure. The solid was then dissolved in DCM and washed with saturated solution of Na$_2$CO$_3$ then water. The organic layer was dried over Na$_2$SO$_4$, filtered and concentrated under reduced pressure. The residue was purified by silica gel chromatography (eluent: heptane/AcOEt 1/0 to 1/1) to afford, after evaporation, 2,4-Bis-{4-[2-(3,4-dimethoxy-phenyl)-2-oxo-ethoxy]-phenyl}-imidazole-1-carboxylic acid tert-butyl in 66% yield.

1H NMR (400 MHz, DMSO-d6) δ ppm 7.98 (s, 1H) 7.79 (d, J=8.9 Hz, 2H) 7.74-7.77 (m, 1H) 7.72-7.74 (m, 1H) 7.49-7.54 (m, 4H) 7.12 (d, J=8.6 Hz, 2H) 7.12 (d, J=8.5 Hz, 2H) 7.03 (d, J=8.8 Hz, 2H) 6.99 (d, J=8.9 Hz, 2H) 5.60 (s, 2H) 5.55 (s, 2H) 3.88 (s, 3H) 3.87 (s, 3H) 3.85 (s, 3H) 3.84 (s, 3H) 1.41 (s, 9H)

LCUV-MS: Rt=2.46 min m/z=709 (method 5)

Example 18: Synthesis of 1-(3,4-Dimethoxy-phenyl)-2-[4-(4-{4-[2-(3,4-dimethoxy-phenyl)-2-oxo-ethoxy]-phenyl}-1H-imidazol-2-yl)-phenoxy]-ethanone Boc protected diketone 15 (1 eq, 0.55 g, 0.78 mmol) was dissolved in 2 mL of DCM then 3.88 mL of a solution of HCl 4N in dioxane (20 eq, 15.52 mmol) was added. The mixture was warmed to 60° C. for 2 h then cooled to room temperature and filtered. Ethyl acetate and a saturated solution of NaHCO$_3$ were added and the suspension was filtered. The solid was washed with water and dried under vacuum at 50° C. 1-(3,4-Dimethoxy-phenyl)-2-[4-(4-{4-[2-(3,4-dimethoxy-phenyl)-2-oxo-ethoxy]-phenyl}-1H-imidazol-2-yl)-phenoxy]-ethanone (compound of formula (II)) was obtained in 79% yield.

1H NMR (400 MHz, DMSO-d6) δ ppm 14.64 (br. s, 2H) 8.15 (d, J=9.0 Hz, 2H) 8.10 (s, 1H) 7.89 (d, J=8.7 Hz, 2H) 7.74 (dd, J=8.4, 1.9 Hz, 2H) 7.50 (d, J=1.9 Hz, 2H) 7.25 (d, J=9.0 Hz, 2H) 7.14 (d, J=8.7 Hz, 2H) 7.13 (d, J=8.4 Hz, 2H) 5.72 (s, 2H) 5.63 (s, 2H) 3.88 (s, 6H) 3.85 (s, 6H)

LCUV-MS: Rt=1.97 min m/z=609 (method 5)

Example 19: Synthesis of 1-(3,4-Dimethoxy-phenyl)-2-[4-(2-{4-[2-(3,4-dimethoxy-phenyl)-2-hydroxy-ethoxy]-phenyl}-1H-imidazol-4-yl)-phenoxy]-ethanol (isomer 1, 2, 3 and 4) compound I-53

To a suspension of the diketone obtained in example 18 (1 eq, 0.15 mg, 0.25 mmol) in MeOH 12 mL NaBH$_4$ (10 eq, 0.093 mg, 2.46 mmol) was added at RT under N$_2$. After 16 h at RT, 5 ml of HCl 1N was then added, the MeOH was evaporated and 15 mL of DCM were added. The organic layer was separated and washed with water. After separation, the organic phase was dried over Na$_2$SO$_4$ filtered and concentrated under reduced pressure. The residue was purified by silica gel chromatography (eluent: DCM/MeOH 1/0 to 95/5) to give 54 mg after evaporation, of 1-(3,4-Dimethoxy-phenyl)-2-[4-(2-{4-[2-(3,4-dimethoxy-phenyl)-2-hydroxy-ethoxy]-phenyl}-1H-imidazol-4-yl)-phenoxy]-ethanol (compound I-53).

Yield: 36%

1H NMR (400 MHz, DMSO-d6) (2 tautomers form) δ ppm 12.34 (s, 0.75H) 12.23 (s, 0.25H) 7.94 (d, J=8.8 Hz, 0.5H) 7.89 (d, J=8.8 Hz, 1.5H) 7.74 (d, J=8.7 Hz, 1.5H) 7.66 (d, J=8.7 Hz, 0.5H) 7.55 (s, 0.75H) 7.28 (s, 0.25H) 7.08-7.05 (m, 2H) 7.02 (d, J=8.8 Hz, 2H) 6.95-7.00 (m, 2H) 6.91-6.95 (m, 4H) 5.56 (d, J=4.7 Hz, 1.5H) 5.53 (d, J=4.7 Hz, 0.5H) 4.88 (quin, J=5.4 Hz, 2H) 4.04 (d, J=5.9 Hz, 2H) 4.01 (d, J=5.9 Hz, 2H) 3.77 (s, 6H) 3.75 (s, 6H)

LCUV-MS: 95.6% purity at 210 Rt=1.42 min m/z=613 (method 2)

Chiral chromatography (Method 2):
isomers 1: 23.7% (purity at 210 nM) Rt=11.5 min.
Isomer 2+3: 49.6% (purity at 210 nM) Rt=13.6 min.
Isomer 4: 26.7% (purity at 210 nM) Rt=16.1 min.

Example 20: Synthesis of 1-(3,4-Dimethoxy-phenyl)-2-[4-(4-{4-[2-(3,4-dimethoxy-phenyl)-2-oxo-ethoxy]-phenyl}-1-methyl-1H-imidazol-2-yl)-phenoxy]-ethanone To a solution of 1-(3,4-Dimethoxy-phenyl)-2-[4-(4-{4-[2-(3,4-dimethoxy-phenyl)-2-oxo-ethoxy]-phenyl}-1H-imidazol-2-yl)-phenoxy]-ethanone obtained in example 18 (1 eq.) solubilized in DMF was added at room temperature 4 eq. of K$_2$CO$_3$. The suspension was stirred 10 min. then appropriate halogenoalkyl derivative (3 eq.) was added and the mixture was warmed to 50-100° C. for 2 h, cooled to room temperature 16 h then warmed at 50-100° C. for 4 h. Water and ethyl acetate were added to the reaction mixture and the aqueous phase was extracted with ethyl acetate. Organic layers were combined and extracted with water and brine then dried with Na$_2$SO$_4$, filtered and concentrated under vacuum pressure. The residue was purified by silica gel chromatography (eluent: CH$_2$Cl$_2$/MeOH 100/0 to 95/5) to afford, after evaporation, 1-(3,4-Dimethoxy-phenyl)-2-[4-(4-{4-[2-(3,4-dimethoxy-phenyl)-2-oxo-ethoxy]-phenyl}-1-methyl-1H-imidazol-2-yl)-phenoxy]-ethanone (compound of formula (II)).

1H NMR (400 MHz, DMSO-d6) δ ppm 7.71-7.77 (m, 2H) 7.67 (d, J=8.7 Hz, 2H) 7.64 (d, J=8.7 Hz, 2H) 7.57 (s, 1H) 7.52 (d, J=1.9 Hz, 1H) 7.50 (d, J=1.9 Hz, 1H) 7.13 (d, J=4.8 Hz, 1H) 7.11 (d, J=4.8 Hz, 1H) 7.07 (d, J=8.8 Hz, 2H) 6.95 (d, J=8.8 Hz, 2H) 5.60 (s, 2H) 5.51 (s, 2H) 3.87 (s, 3H) 3.87 (s, 3H) 3.85 (s, 3H) 3.84 (s, 3H) 3.73 (s, 3H)

LCUV-MS: 99.3% (UV purity at 220 nm) Rt=1.45 min m/z=627 (method 1)

Example 21: Synthesis of 1-(3,4-Dimethoxy-phenyl)-2-[4-(4-{4-[2-(3,4-dimethoxy-phenyl)-2-hydroxy-ethoxy]-phenyl}-1-methyl-1H-imidazol-2-yl)-phenoxy]-ethanol compound I-58

The reduction method using NaBH$_4$ in route 1 was used in order to obtain I-58 as racemic mixture starting from 1-(3,4-Dimethoxy-phenyl)-2-[4-(4-{4-[2-(3,4-dimethoxy-phenyl)-2-oxo-ethoxy]-phenyl}-1-methyl-1H-imidazol-2-yl)-phenoxy]-ethanone 1H NMR (400 MHz, DMSO-d6) δ ppm 7.67 (d, J=8.7 Hz, 2H) 7.63 (d, J=8.7 Hz, 2H) 7.54 (s, 1H) 7.02-7.09 (m, 4H) 6.89-7.00 (m, 6H) 5.57 (d, J=4.7 Hz, 1H) 5.52 (d, J=4.5 Hz, 1H) 4.82-4.92 (m, 2H) 4.06 (d, J=5.8 Hz, 2H) 4.00 (d, J=5.8 Hz, 2H) 3.77 (s, 3H) 3.77 (s, 3H) 3.75 (s, 3H) 3.74 (s, 3H) 3.72 (s, 3H)

LCUV-MS: 99.3% purity at 220 nM Rt=1.45 min m/z=627 (method 1)

Chiral chromatography (Method 2):
Isomer 1: 24.6% (purity at 210 nM) Rt=12.1 min.
Isomer 2: 25.3% (purity at 210 nM) Rt=13.3 min.
Isomer 3: 24.6% (purity at 210 nM) Rt=15.3 min.
Isomer 4: 25.5% (purity at 210 nM) Rt=16.9 min.

Preparation of Heterocycles

Example 22: Synthesis of 2,4-Bis-(4-methoxy-phenyl)-thiazole 5 g of 4-methoxythiobenzamide (1 eq, 29.9 mmol) and 6.85 g of 2-bromo-1-(4-methoxyphenyl)-ethanone (1 eq, 29.9 mmol) were dissolved in 40 mL of EtOH and heated at reflux for 2 h. After cooled down to RT over a 2 h period the solid formed was filtered off, washed with a minimum of EtOH and dried under vacuum at 40° C. overnight. 7.32 g of compound 2,4-Bis-(4-methoxy-phenyl)-thiazole were obtained (82% yield).

1H NMR (250 MHz, DMSO-d6) δ ppm 7.97 (d, J=8.8 Hz, 2H) 7.96 (d, J=8.8 Hz, 2H) 7.91 (s, 1H) 7.08 (d, J=8.8 Hz, 2H) 7.03 (d, J=8.8 Hz, 2H) 3.84 (s, 3H) 3.81 (s, 3H)

LCUV-MS: Rt=6.57 min, m/z=298, UV (220) purity=97.7% (method 5)

Example 23: Synthesis of 3-Chloro-4-(4-methoxy-phenyl)-thiophene 20

10.68 mL of Dichlorothiophene 19 (1 eq, 98.62 mmol) were dissolved in 50 mL of DCM then 32.32 mL of methoxybenzene (3 eq, 295.86 mmol) were added and stirred at 0° C. 12.49 g of AlCl₃ (0.95 eq, 93.69 mmol) were added at this temperature by portions and the mixture stirred at 5° C. for 1 h then warm to RT for 4 h. The reaction mixture was poured onto water/ice and extract with DCM. The organic layers were combined and washed with 5% solution of NaHCO₃ in water, water and brine. The organic layer was dried over Na₂SO₄, filtered and concentrated under reduced pressure. The residue was purified by silica gel chromatography (eluent: AcOEt/heptane 0/1 to 3/7) to afford, after evaporation, 8.83 g of 3-Chloro-4-(4-methoxy-phenyl)-thiophene (40% yield).

1H NMR (250 MHz, DMSO-d6) δ ppm 7.63 (d, J=8.8 Hz, 2H) 7.63 (d, J=1.8 Hz, 1H) 7.57 (d, J=1.8 Hz, 1H) 6.97 (d, J=8.8 Hz, 2H) 3.78 (s, 3H)

LCUV-MS: Rt=2.64 min m/z=225 (method 5)

Example 24: Synthesis of 2,4-Bis-(4-methoxy-phenyl)-thiophene 21

In a sealed tube 3.33 g of 3-Chloro-4-(4-methoxy-phenyl)-thiophene obtained in example 23 (1 eq, 14.84 mmol) was dissolved in 50 mL of dioxane then 4.51 g of 4-methoxyphenyl boronic acid (2 eq, 29.68 mmol), 25 mL of H₂O (93.5 eq, 1387.7 mmol) and 9.67 g of Cs₂CO₃ (2 eq, 29.68 mmol) were added at RT. The mixture under Ar was warmed to 100° C. for 6 h and cooled 18 h to RT. The precipitate was filtered and washed with AcOEt, H₂O and MeOH. The solid was dried overnight under vacuum pressure at 50° C. to afford 3 g of 2,4-Bis-(4-methoxy-phenyl)-thiophene (68% yield).

1H NMR (250 MHz, DMSO-d6) δ ppm 7.79 (d, J=1.5 Hz, 1H) 7.70 (d, J=8.9 Hz, 2H) 7.65 (d, J=8.9 Hz, 2H) 7.63 (d, J=1.5 Hz, 1H) 7.01 (d, J=4.2 Hz, 2H) 6.98 (d, J=4.2 Hz, 2H) 3.80 (s, 3H) 3.79 (s, 3H)

LCUV-MS: Rt=2.76 min m/z=297 (method 5)

Example 25: Synthesis of 3,5-Bis-(4-benzyloxy-phenyl)-[1,2,4]oxadiazole 23

To 5 g of the commercially available 4-Benzyloxy-benzonitrile 22 (1 eq, 23.9 mmol) in 10 mL of ethylene glycole were added 1.52 g of Na₂CO₃ (0.6 eq, 14.34 mmol), 1.29 mL of water (3 eq, 71.69 mmol) and 0.83 mg of hydroxylamine hydrochloride (0.5 eq, 11.95 mmol) in a sealed tube. The mixture was warmed to 195° C. for 24 h then water was added and the suspension was filtered. The solid was washed with water and dried under vacuum pressure at 50° C. The solid was triturated with MeOH, filtered and dried under vacuum pressure at 40° C. 3,5-Bis-(4-benzyloxy-phenyl)-[1,2,4]oxadiazole was obtained in 37% yield.

1H NMR (400 MHz, DMSO-d6) δ ppm 8.13 (d, J=8.7 Hz, 2H) 8.02 (d, J=8.7 Hz, 2H) 7.32-7.54 (m, 10H) 7.28 (d, J=8.7 Hz, 2H) 7.22 (d, J=8.7 Hz, 2H) 5.25 (s, 2H) 5.21 (s, 2H)

LCUV-MS: Rt=3.1 min m/z=435 (method 5)

Example 26: Synthesis of 2,5-Bis-(4-methoxy-phenyl)-oxazole 26

1 g of commercially available 5-4-Methoxyphenyl)-oxazole 24 (1 eq, 5.71 mmol) was dissolved in 12 mL of DMF under Ar at RT. Then 1.2 g of 1-bromo-4-methoxyphenyl 25 (1.2 eq, 6.85 mmol), 1.58 g of K₂CO₃ (2 eq, 11.42 mmol), 64.1 mg of Pd(OAc)₂ (0.05 eq, 0.29 mmol) and 1.09 g of CuI (1 eq, 5.71 mmol) were added and the reaction mixture was warmed to 140° C. for 6H. The mixture was cooled and filtered through celite washed with AcOEt. The organic layer was washed with H₂O then brine then dried over Na₂SO₄, filtered and concentrated under reduced pressure. The residue was purified by silica gel chromatography (eluent: DCM/MeOH 100/0 to 95/5) to afford, after evaporation, 580 mg of 2,5-Bis-(4-methoxy-phenyl)-oxazole (36% yield).

1H NMR (250 MHz, DMSO-d6) δ ppm 8.00 (d, J=8.9 Hz, 2H) 7.75 (d, J=8.9 Hz, 2H) 7.61 (s, 1H) 7.10 (d, J=8.9 Hz, 2H) 7.06 (d, J=8.9 Hz, 2H) 3.84 (s, 3H) 3.82 (s, 3H)

LCUV-MS: Rt=9.22 min purity (UV 220 nm) 97% MH⁺=282 (Method 1)

The table below illustrates the chemical structures and the physical properties of some examples of compounds according to the invention.

In general, a reaction mixture containing a final compound of the formula (I) or an intermediate is worked up and, if desired, the product is then purified by customary processes known to those skilled in the art. For example, a synthesized compound can be purified using well known methods such as crystallization, chromatography or reverse phase-high performance liquid chromatography (RP-HPLC) or other methods of separation based, for example, on the size, charge or hydrophobicity of the compound. Similarly, well known methods such as NMR, IR and mass spectrometry (MS) can be used for characterizing a compound of the invention.

The compounds of the formula (I), which on account of their chemical structure occur in enantiomeric or diastereomeric forms, can be prepared in enantiomeric pure form employing enantiomerically pure starting material or can be resolved into the pure enantiomers by chromatography on chiral stationary phases or derivatization by means of chiral enantiomerically pure compounds such as amino acids, separation of the diastereomers thus obtained, and removal of the chiral auxiliary groups.

It is to be noted that, when the compounds were prepared using a chiral reductive catalyst (as described in scheme 1) their chiral configuration was not determined via direct analytical methods. Therefore when different isomers of the same compound were obtained, they were named "isomer 1", "isomer 2" . . . . However, it is well known that the asymmetric catalysts 4a, 4b which were used lead to final compounds having the same chirality as said catalysts.

Column "chiral agent" precises the agent used during the reduction step from compound of formula (II) or (III) into compound of formula (I)

| N° | Name and Isomeric form | Chiral chromatography | | LCUVMS | | | COMMENTS | Scheme | Chiral agent |
|---|---|---|---|---|---|---|---|---|---|
| | | Chiral Purity (%) | Rt(min.) | UV purity (%) | Rt (min.) | m/z | | | |
| I-1 | 1-(3,4-dimethoxyphenyl)-2-[4-[2-[4-[2-(3,4-dimethoxyphenyl)-2-hydroxy-ethoxy]phenyl]-5-methyl-oxazol-4-yl]phenoxy]ethanol (equimolar mixture of 4 isomers) | | | 98.3 | 8.68 | 628 | equimolar mixture of 4 isomers | 1 | NaBH$_4$ |
| I-2 | 1-(3,4-dimethoxyphenyl)-2-[4-[2-[4-[2-(3,4-dimethoxyphenyl)-2-hydroxy-1,1-dimethyl-ethoxy]phenyl]-5-methyl-oxazol-4-yl]phenoxy]-2-methyl-propan-1-ol (equimolar mixture of 4 isomers) | | | 97.7 | 9.93 | 684 | equimolar mixture of 4 isomers | 1 | NaBH$_4$ |
| I-3 | 1-(3,4-dimethoxyphenyl)-2-[4-[2-[4-[2-(3,4-dimethoxyphenyl)-2-hydroxy-1,1-dimethyl-ethoxy]phenyl]-5-methyl-oxazol-4-yl]phenoxy]-2-methyl-propan-1-ol (isomer 2) | 99.8 | 4.9 | 96.8 | 2.85 | 684 | 1 major isomer | 1 | 4a |
| I-4 | 1-(3,4-dimethoxyphenyl)-2-[4-[2-[4-[2-(3,4-dimethoxyphenyl)-2-hydroxy-1,1-dimethyl-ethoxy]phenyl]-5-methyl-oxazol-4-yl]phenoxy]-2-methyl-propan-1-ol (isomer 1) | 98.3 | 16.6 | 94.5 | 2.85 | 684 | 1 major isomer | 1 | 4b |
| I-5 | 1-(3,4-dimethoxyphenyl)-2-[4-[2-[4-[2-(3,4-dimethoxyphenyl)-2-hydroxy-ethoxy]phenyl]-4-methyl-oxazol-5-yl]phenoxy]ethanol (isomer 1) | 100 | 8.9 | 94.9 | 8.3 | 628 | 1 major isomer | 1 | 4b |
| I-6 | 1-(3,4-dimethoxyphenyl)-2-[4-[2-[4-[2-(3,4-dimethoxyphenyl)-2-hydroxy-1,1-dimethyl-ethoxy]phenyl]-5-methyl-thiazol-4-yl]phenoxy]-2-methyl-propan-1-ol (equimolar mixture of 4 isomers) | | | 98.9 | 10.35 | 700 | equimolar mixture of 4 isomers | 1 | NaBH$_4$ |
| I-7 | 1-(3,4-dimethoxyphenyl)-2-[4-[2-[4-[2-(3,4-dimethoxyphenyl)-2- | | | 97.3 | 9.05 | 644 | equimolar mixture of 4 isomers | | NaBH$_4$ |

-continued

| | | Chiral chromatography | | LCUVMS | | | | | |
|---|---|---|---|---|---|---|---|---|---|
| N° | Name and Isomeric form | Chiral Purity (%) | Rt(min.) | UV purity (%) | Rt (min.) | m/z | COMMENTS | Scheme | Chiral agent |
| | hydroxy-ethoxy]phenyl]-5-methyl-thiazol-4-yl]phenoxy]ethanol (equimolar mixture of 4 isomers) | | | | | | | | |
| I-8 | 1-(3,4-dimethoxyphenyl)-2-[4-[2-[4-[2-(3,4-dimethoxyphenyl)-2-hydroxy-1,1-dimethyl-ethoxy]phenyl]-5-methyl-thiazol-4-yl]phenoxy]-2-methyl-propan-1-ol (isomer 2) | 98.9 | 4.3 | 97.9 | 10.36 | 700 | 1 major isomer | 1 | 4a |
| I-9 | 1-(3,4-dimethoxyphenyl)-2-[4-[2-[4-[2-(3,4-dimethoxyphenyl)-2-hydroxy-1,1-dimethyl-ethoxy]phenyl]-5-methyl-thiazol-4-yl]phenoxy]-2-methyl-propan-1-ol (isomer 1) | 98.7 | 10.3 | 98.1 | 10.36 | 700 | 1 major isomer | 1 | 4b |
| I-10 | 1-(3,4-dimethoxyphenyl)-2-[4-[2-[4-[2-(3,4-dimethoxyphenyl)-2-hydroxy-ethoxy]phenyl]-5-methyl-thiazol-4-yl]phenoxy]ethanol (isomer 1) | 99.1 | 3.4 | 96.3 | 2.5 | 644 | 1 major isomer | 1 | 4b |
| I-11 | 1-(3,4-dimethoxyphenyl)-2-[4-[2-[4-[2-(3,4-dimethoxyphenyl)-2-hydroxy-ethoxy]phenyl]-5-methyl-thiazol-4-yl]phenoxy]ethanol (isomer 2) | 94.8 | 7.2 | 96.8 | 2.5 | 644 | 1 major isomer | 1 | 4a |
| I-12 | 1-(3,4-dimethoxyphenyl)-2-[4-[2-[4-[2-(3,4-dimethoxyphenyl)-2-hydroxy-1-methyl-ethoxy]phenyl]oxazol-4-yl]phenoxy]propan-1-ol (mixture of isomers) | | | 90.4 | 8.98 | 642 | mixture of isomers | 1 | NaBH$_4$ |
| I-13 | 1-(3,4-dimethoxyphenyl)-2-[4-[2-[4-[2-(3,4-dimethoxyphenyl)-2-hydroxy-ethoxy]phenyl]oxazol-4-yl]phenoxy]ethanol (isomer 2) | 90.9 | 4 | 100% 98.4 | 5 MIN-UTES 8.43 | 614.51 614 | 1 major isomer | 1 | 4a |
| I-14 | 1-(3,4-dimethoxyphenyl)-2-[4-[2-[4-[2-(3,4-dimethoxyphenyl)-2-hydroxy-ethoxy]phenyl]oxazol-4-yl]phenoxy]ethanol (isomer 1) | 80.2 | 2.8 | 91.1 | 8.44 | 614 | 1 major isomer | 1 | 4b |
| I-15 | 1-(4-chloro-3-methoxy-phenyl)-2-[4-[2-[4-[2-(4-chloro-3-methoxy-phenyl)-2-hydroxy-ethoxy]phenyl]oxazol-4-yl]phenoxy]ethanol (equimolar mixture of 4 isomers) | | | 98.5 | 10.64 | 622.2 | equimolar mixture of 4 isomers | 1 | NaBH$_4$ |

-continued

| N° | Name and Isomeric form | Chiral chromatography | | LCUVMS | | | | Scheme | Chiral agent |
|---|---|---|---|---|---|---|---|---|---|
| | | Chiral Purity (%) | Rt(min.) | UV purity (%) | Rt (min.) | m/z | COMMENTS | | |
| I-16 | 1-(4-fluoro-3-methoxy-phenyl)-2-[4-[2-[4-[2-(4-fluoro-3-methoxy-phenyl)-2-hydroxy-ethoxy]phenyl]oxazol-4-yl]phenoxy]ethanol (equimolar mixture of 4 isomers) | | | 93.4 | 9.41 | 590.2 | equimolar mixture of 4 isomers | 1 | NaBH$_4$ |
| I-17 | 1-(3-fluoro-4-methoxy-phenyl)-2-[4-[2-[4-[2-(3-fluoro-4-methoxy-phenyl)-2-hydroxy-ethoxy]phenyl]oxazol-4-yl]phenoxy]ethanol (equimolar mixture of 4 isomers) | | | 97.1 | 9.28 | 590.2 | equimolar mixture of 4 isomers | 1 | NaBH$_4$ |
| I-18 | 1-(3,4-dimethoxyphenyl)-2-[4-[2-[4-[2-(3,4-dimethoxyphenyl)-2-hydroxy-1,1-dimethyl-ethoxy]phenyl]oxazol-4-yl]phenoxy]-2-methyl-propan-1-ol (isomer 2) | 100 | 15.2 | 98.6 | 9.64 | 670 | 1 major isomer | 1 | 4a |
| I-19 | 1-(3,4-dimethoxyphenyl)-2-[4-[2-[4-[2-(3,4-dimethoxyphenyl)-2-hydroxy-1,1-dimethyl-ethoxy]phenyl]oxazol-4-yl]phenoxy]-2-methyl-propan-1-ol (isomer 1) | 100 | 21.3 | 98.2 | 9.65 | 670 | 1 major isomer | 1 | 4b |
| I-20 | 2-[4-[2-[4-[2-hydroxy-2-(3,4,5-trimethoxyphenyl)ethoxy]phenyl]oxazol-4-yl]phenoxy]-1-(3,4,5-trimethoxyphenyl)ethanol (equimolar mixture of 4 isomers) | | | 97.7 | 8.6 | 674 | equimolar mixture of 4 isomers | 1 | NaBH$_4$ |
| I-21 | 2-[4-[2-[4-[2-hydroxy-2-(3,4,5-trimethoxyphenyl)ethoxy]phenyl]oxazol-4-yl]phenoxy]-1-(3,4,5-trimethoxyphenyl)ethanol (isomer 1) | 88.1 | 7.1 | 95.1 | 8.6 | 674 | 1 major isomer | 1 | 4b |
| I-22 | 2-[4-[2-[4-[2-hydroxy-2-(3,4,5-trimethoxyphenyl)ethoxy]phenyl]oxazol-4-yl]phenoxy]-1-(3,4,5-trimethoxyphenyl)ethanol (isomer 2) | 42.8 | 13.4 | 98.3 | 8.56 | 674 | 1 major isomer | 1 | 4a |
| I-23 | 1-(3,4-dimethoxyphenyl)-2-[4-[2-[4-[2-(3,4-dimethoxyphenyl)-2-hydroxy-ethoxy]phenyl]thiazol-4-yl]phenoxy]ethanol (isomer 2) | 95.2 | 4.1 | 98.3 | 9.22 | 630 | 1 major isomer | 1 | 4a |
| I-69 | 1-(3,4-dimethoxyphenyl)-2-[4-[2-[4-[2-(3,4-dimethoxyphenyl)-2-hydroxy-ethoxy]phenyl]thiazol-4-yl]phenoxy]ethanol (isomer 1, 2, 3, and 4) | | | 99.1 | 18.44 | 630 | equimolar mixture of 4 isomers | 1 | NaBH$_4$ |
| I-24 | 1-(3,4-dimethoxyphenyl)-2-[4- | 95.5 | 4.2 | 98.9 | 8.88 | 630 | 1 major isomer | 1 | 4b |

-continued

| N° | Name and Isomeric form | Chiral chromatography | | LCUVMS | | | COMMENTS | Scheme | Chiral agent |
|---|---|---|---|---|---|---|---|---|---|
| | | Chiral Purity (%) | Rt(min.) | UV purity (%) | Rt (min.) | m/z | | | |
| | [2-[4-[2-(3,4-dimethoxyphenyl)-2-hydroxy-ethoxy]phenyl]thiazol-4-yl]phenoxy]ethanol (isomer 1) | | | | | | | | |
| I-25 | 1-(3,4-dimethoxyphenyl)-2-[4-[2-[4-[2-(3,4-dimethoxyphenyl)-2-hydroxy-ethoxy]phenyl]thiazol-4-yl]phenoxy]ethanol (isomer 3 and 4) | | | 98.8 | 8.8 | 630 | Racemic: 2 enantiomers | 1* | NaBH$_4$ |
| I-26 | 1-(3,4-dimethoxyphenyl)-2-[4-[2-[4-[2-(3,4-dimethoxyphenyl)-2-hydroxy-1,1-dimethyl-ethoxy]phenyl]thiazol-4-yl]phenoxy]-2-methyl-propan-1-ol (equimolar mixture of 4 isomers) | | | 98.31 | 21.7 | 686 | equimolar mixture of 4 isomers | 1 | NaBH$_4$ |
| I-27 | 1-(3,4-dimethoxyphenyl)-2-[4-[2-[4-[2-(3,4-dimethoxyphenyl)-2-hydroxy-1,1-dimethyl-ethoxy]phenyl]thiazol-4-yl]phenoxy]-2-methyl-propan-1-ol | 80.7 | 4.9 | 97.4 | 10.09 | 686 | 1 major isomer | 1 | 4a |
| I-28 | 1-(3,4-dimethoxyphenyl)-2-[4-[2-[4-[2-(3,4-dimethoxyphenyl)-2-hydroxy-1,1-dimethyl-ethoxy]phenyl]thiazol-4-yl]phenoxy]-2-methyl-propan-1-ol (isomer 1) | 81.8 | 10.4 | 97.3 | 10.08 | 686 | 1 major isomer | 1 | 4b |
| I-29 | 1-(3,4-dimethoxyphenyl)-2-[4-[2-[4-[2-(3,4-dimethoxyphenyl)-2-hydroxy-1-methyl-ethoxy]phenyl]thiazol-4-yl]phenoxy]propan-1-ol (isomer 6) | 99.8 | 15.4 | | | | 1 major isomer | 1** | NaBH$_4$ |
| I-30 | 1-(3,4-dimethoxyphenyl)-2-[4-[2-[4-[2-(3,4-dimethoxyphenyl)-2-hydroxy-1-methyl-ethoxy]phenyl]thiazol-4-yl]phenoxy]propan-1-ol (isomer 2) | 91.1 | 9.9 | 100 | 19.98 | 658 | 1 major isomer | 1** | NaBH$_4$ |
| I-31 | 1-(3,4-dimethoxyphenyl)-2-[4-[2-[4-[2-(3,4-dimethoxyphenyl)-2-hydroxy-1-methyl-ethoxy]phenyl]thiazol-4-yl]phenoxy]propan-1-ol (isomer 3) | 95.9 | 11.1 | 99.5<br>99.2 | 20.08<br>20.07 | 658<br>658 | 1 major isomer | 1** | NaBH$_4$ |
| I-32 | 1-(3,4-dimethoxyphenyl)-2-[4-[2-[4-[2-(3,4-dimethoxyphenyl)-2-hydroxy-1-methyl-ethoxy]phenyl]thiazol-4-yl]phenoxy]propan-1-ol (isomer 4) | 64.8 | 10.5 | 97.8 | 9.4 | 658 | 1 major isomer | 1** | NaBH$_4$ |

-continued

| N° | Name and Isomeric form | Chiral chromatography | | LCUVMS | | | | Scheme | Chiral agent |
|---|---|---|---|---|---|---|---|---|---|
| | | Chiral Purity (%) | Rt(min.) | UV purity (%) | Rt (min.) | m/z | COMMENTS | | |
| I-33 | 1-(3,4-dimethoxyphenyl)-2-[4-[2-[4-[2-(3,4-dimethoxyphenyl)-2-hydroxy-1-methyl-ethoxy]phenyl]thiazol-4-yl]phenoxy]propan-1-ol (isomer 5) | 98.5 | 12.9 | 100 | 20.08 | 658 | 1 major isomer | 1** | NaBH$_4$ |
| I-61 | 1-(3,4-dimethoxyphenyl)-2-[4-[2-[4-[2-(3,4-dimethoxyphenyl)-2-hydroxy-ethoxy]phenyl]thiazol-4-yl]phenoxy]ethanol (isomer 3) | 82.2 | 11.4 | 99.4 | 2.39 | 630 | 1 major isomer | 2 | First reduction 4b then 4a |
| I-62 | 1-(3,4-dimethoxyphenyl)-2-[4-[2-[4-[2-(3,4-dimethoxyphenyl)-2-hydroxy-ethoxy]phenyl]thiazol-4-yl]phenoxy]ethanol (isomer 4) | 88.2 | 22.7 | 98.5 | 2.38 | 630 | 1 major isomer | 2 | First reduction 4a then 4b |
| I-63 | 1-(3,4-dimethoxyphenyl)-2-[4-[4-[4-[2-(3,4-dimethoxyphenyl)-2-hydroxy-ethoxy]phenyl]thiazol-2-yl]phenoxy]-2-methyl-propan-1-ol (equimolar mixture of 4 isomers) | | | 99.25 | 2.62 | 658 | equimolar mixture of 4 isomers | 2 | NaBH$_4$ |
| I-64 | 1-(3,4-dimethoxyphenyl)-2-[4-[2-[4-[2-(3,4-dimethoxyphenyl)-2-hydroxy-ethoxy]phenyl]thiazol-4-yl]phenoxy]-2-methyl-propan-1-ol (equimolar mixture of 4 isomers) | | | 100 | 2.61 | 658 | equimolar mixture of 4 isomers | 2 | NaBH$_4$ |
| I-65 | 1-(3,4-dimethoxyphenyl)-2-[4-[4-[4-[2-(3,4-dimethoxyphenyl)-2-hydroxy-ethoxy]phenyl]thiazol-2-yl]phenoxy]-2-methyl-propan-1-ol (isomer 2) | 94 | 6.3 | 99.5 | 2.61 | 658 | 1 major isomer | 2 | First reduction 4a then 4a |
| I-66 | 1-(3,4-dimethoxyphenyl)-2-[4-[4-[4-[2-(3,4-dimethoxyphenyl)-2-hydroxy-ethoxy]phenyl]thiazol-2-yl]phenoxy]-2-methyl-propan-1-ol (isomer 1) | 95.4 | 11.5 | 100 | 2.61 | 658 | 1 major isomer | 2 | First reduction 4b then 4b |
| I-67 | 1-(3,4-dimethoxyphenyl)-2-[4-[2-[4-[2-(3,4-dimethoxyphenyl)-2-hydroxy-ethoxy]phenyl]thiazol-4-yl]phenoxy]-2-methyl-propan-1-ol (isomer 2) | 97.4 | 6.6 | 97.6 | 2.61 | 658 | 1 major isomer | 2 | First reduction 4a then 4a |
| I-68 | 1-(3,4-dimethoxyphenyl)-2-[4-[2-[4-[2-(3,4-dimethoxyphenyl)-2-hydroxy-ethoxy]phenyl]thiazol-4- | 98 | 13.3 | 97.4 | 2.64 | 658 | 1 major isomer | 2 | First reduction 4b then 4b |

-continued

|  |  | Chiral chromatography | | LCUVMS | | | | |
| --- | --- | --- | --- | --- | --- | --- | --- | --- |
| N° | Name and Isomeric form | Chiral Purity (%) | Rt(min.) | UV purity (%) | Rt (min.) | m/z | COMMENTS | Scheme | Chiral agent |
| I-34 | yl]phenoxy]-2-methyl-propan-1-ol (isomer 1) 1-(3,4-dimethoxyphenyl)-2-[4-[5-[4-[2-(3,4-dimethoxyphenyl)-2-hydroxy-1,1-dimethyl-ethoxy]phenyl]-3-thienyl]phenoxy]-2-methyl-propan-1-ol (equimolar mixture of 4 isomers) |  |  | 99 | 10.33 | 685 | equimolar mixture of 4 isomers | 1 | NaBH$_4$ |
| I-35 | 1-(3,4-dimethoxyphenyl)-2-[4-[5-[4-[2-(3,4-dimethoxyphenyl)-2-hydroxy-ethoxy]phenyl]-3-thienyl]phenoxy]ethanol (equimolar mixture of 4 isomers) |  |  | 99.6 | 9.1 | 629 | equimolar mixture of 4 isomers | 1 | NaBH$_4$ |
| I-36 | 1-(3,4-dimethoxyphenyl)-2-[4-[5-[4-[2-(3,4-dimethoxyphenyl)-2-hydroxy-ethoxy]phenyl]-1,2,4-oxadiazol-3-yl]phenoxy]ethanol (equimolar mixture of 4 isomers) |  |  | 98.9 | 8.56 | 615 | equimolar mixture of 4 isomers | 1 | NaBH$_4$ |
| I-37 | 1-(3,4-dimethoxyphenyl)-2-[4-[5-[4-[2-(3,4-dimethoxyphenyl)-2-hydroxy-1,1-dimethyl-ethoxy]phenyl]-1,2,4-oxadiazol-3-yl]phenoxy]-2-methyl-propan-1-ol (isomer 1) | 98.1 | 3.7 | 100 | 2.71 | 671 | 1 major isomer | 1 | 4b |
| I-38 | 1-(3,4-dimethoxyphenyl)-2-[4-[5-[4-[2-(3,4-dimethoxyphenyl)-2-hydroxy-11-dimethyl-ethoxy]phenyl]-1,2,4-oxadiazol-3-yl]phenoxy]-2-methyl-propan-1-ol (isomer 2) | 96.7 | 3 | 100 | 2.71 | 671 | 1 major, isomer | 1 | 4a |
| I-39 | 1-(3,4-dimethoxyphenyl)-2-[4-[5-[4-[2-(3,4-dimethoxyphenyl)-2-hydroxy-1-methyl-ethoxy]phenyl]-1,2,4-thiadiazol-3-yl]phenoxy]propan-1-ol (mixture of isomers) |  |  | 97.6 | 19.98 | 659.3 | mixture of isomers | 1 | NaBH$_4$ |
| I-40 | 1-(3,4-dimethoxyphenyl)-2-[4-[5-[4-[2-(3,4-dimethoxyphenyl)-2-hydroxy-ethoxy]phenyl]-1,2,4-thiadiazol-3-yl]phenoxy]ethanol (isomer 2) | 93.5 | 15.5 | 98.7 | 18.5 | 631 | 1 major isomer | 1 | 4a |
| I-41 | 1-(3,4-dimethoxyphenyl)-2-[4-[5-[4-[2-(3,4-dimethoxyphenyl)-2-hydroxy-ethoxy]phenyl]- | 96.5 | 11.7 | 99.3 | 18.5 | 631 | 1 major isomer | 1 | 4b |

|  |  | Chiral chromatography | | LCUVMS | | | | | |
| --- | --- | --- | --- | --- | --- | --- | --- | --- | --- |
| N° | Name and Isomeric form | Chiral Purity (%) | Rt(min.) | UV purity (%) | Rt (min.) | m/z | COMMENTS | Scheme | Chiral agent |
|  | 1,2,4-thiadiazol-3-yl]phenoxy]ethanol (isomer 1) | | | | | | | | |
| I-42 | 1-(3,4-dimethoxyphenyl)-2-[4-[5-[4-[2-(3,4-dimethoxyphenyl)-2-hydroxy-1,1-dimethyl-ethoxy]phenyl]-1,2,4-thiadiazol-3-yl]phenoxy]-2-methyl-propan-1-ol (equimolar mixture of 4 isomers) | | | 97.4 | 10.21 | 687 | equimolar mixture of 4 isomers | 1 | $NaBH_4$ |
| I-43 | 1-(3,4-dimethoxyphenyl)-2-[4-[5-[4-[2-(3,4-dimethoxyphenyl)-2-hydroxy-1,1-dimethyl-ethoxy]phenyl]-1,2,4-thiadiazol-3-yl]phenoxy]-2-methyl-propan-1-ol (isomer 2) | 99.7 | 6.3 | 98.2 | 2.87 | 687 | 1 major isomer | 1 | 4a |
| I-44 | 1-(3,4-dimethoxyphenyl)-2-[4-[5-[4-[2-(3,4-dimethoxyphenyl)-2-hydroxy-1,1-dimethyl-ethoxy]phenyl]-1,2,4-thiadiazol-3-yl]phenoxy]-2-methyl-propan-1-ol (isomer 1) | 97.8 | 19 | 98.3 | 2.87 | 687 | 1 major isomer | 1 | 4b |
| I-45 | 1-(3,4-dimethoxyphenyl)-2-[4-[2-[4-[2-(3,4-dimethoxyphenyl)-2-hydroxy-1-methyl-ethoxy]phenyl]oxazol-5-yl]phenoxy]propan-1-ol (mixture of isomers) | | | 97.5 | 8.67 | 642 | mixture of isomers | 1 | $NaBH_4$ |
| I-53 | 1-(3,4-dimethoxyphenyl)-2-[4-[2-[4-[2-(3,4-dimethoxyphenyl)-2-hydroxy-ethoxy]phenyl]-1H-imidazol-4-yl]phenoxy]ethanol (equimolar mixture of 4 isomers) | | | 95.6 | 1.42 | 613 | equimolar mixture of 4 isomers | 3 | $NaBH_4$ |
| I-54 | 1-(3,4-dimethoxyphenyl)-2-[4-[2-[4-[2-(3,4-dimethoxyphenyl)-2-hydroxy-1,1-dimethyl-ethoxy]phenyl]-1H-imidazol-4-yl]phenoxy]-2-methyl-propan-1-ol (equimolar mixture of 4 isomers) | | | 98.6 | 1.71 | 669 | equimolar mixture of 4 isomers | 3 | $NaBH_4$ |
| I-55 | 1-(3,4-dimethoxyphenyl)-2-[4-[2-[4-[2-(3,4-dimethoxyphenyl)-2-hydroxy-1,1-dimethyl-ethoxy]phenyl]-1H-imidazol-4-yl]phenoxy]-2-methyl-propan-1-ol (isomer 1) | 94.8 | 15.8 | 94.05 | 1.7 | 669 | 1 major isomer | 3 | 4b |
| I-56 | 1-(3,4-dimethoxyphenyl)-2-[4-[2-[4-[2-(3,4-dimethoxyphenyl)-2-hydroxy-1,1-dimethyl- | 95.2 | 5 | 92.06 | 1.71 | 669 | 1 major isomer | 3 | 4a |

-continued

| N° | Name and Isomeric form | Chiral Purity (%) | Rt(min.) | UV purity (%) | Rt (min.) | m/z | COMMENTS | Scheme | Chiral agent |
|---|---|---|---|---|---|---|---|---|---|
| | ethoxy]phenyl]-1H-imidazol-4-yl]phenoxy]-2-methyl-propan-1-ol (isomer 2) | | | | | | | | |
| I-57 | 1-(3,4-dimethoxyphenyl)-2-[4-[2-[4-[2-(3,4-dimethoxyphenyl)-2-hydroxy-1,1-dimethyl-ethoxy]phenyl]-1-methyl-imidazol-4-yl]phenoxy]-2-methyl-propan-1-ol (equimolar mixture of 4 isomers) | | | 94.23 | 1.76 | 683 | equimolar mixture of 4 isomers | 3 | NaBH$_4$ |
| I-58 | 1-(3,4-dimethoxyphenyl)-2-[4-[2-[4-[2-(3,4-dimethoxyphenyl)-2-hydroxy-ethoxy]phenyl]-1-methyl-imidazol-4-yl]phenoxy]ethanol (equimolar mixture of 4 isomers) | | | 99.3 | 1.45 | 627 | equimolar mixture of 4 isomers | 3 | NaBH$_4$ |
| I-59 | 1-(3,4-dimethoxyphenyl)-2-[4-[2-[4-[2-(3,4-dimethoxyphenyl)-2-hydroxy-1,1-dimethyl-ethoxy]phenyl]-1-(2-morpholinoethyl)imidazol-4-yl]phenoxy]-2-methyl-propan-1-ol (equimolar mixture of 4 isomers) | | | 100 | 1.68 | 782 | equimolar mixture of 4 isomers | 3 | NaBH$_4$ |
| I-60 | 1-(3,4-dimethoxyphenyl)-2-[4-[2-[4-[2-(3,4-dimethoxyphenyl)-2-hydroxy-ethoxy]phenyl]-1-(2-morpholinoethyl)imidazol-4-yl]phenoxy]ethanol hydrochloride (equimolar mixture of 4 isomers) | | | 95.7 | 1.37 | 726 | equimolar mixture of 4 isomers | 3 | NaBH$_4$ |
| I-46 | 1-(3,4-dimethoxyphenyl)-2-[4-[2-[4-[2-(3,4-dimethoxyphenyl)-2-hydroxy-ethoxy]phenyl]-4-methyl-oxazol-5-yl]phenoxy]ethanol (isomer 2) | 89.1 | 13.8 | 95 | 8.3 | 628 | 1 major isomer | 3 | 4a |
| I-47 | 1-(3,4-dimethoxyphenyl)-2-[4-[5-[4-[2-(3,4-dimethoxyphenyl)-2-hydroxy-ethoxy]phenyl]-1,2,4-oxadiazol-3-yl]phenoxy]ethanol (isomer 1) | 97.2 | 10.6 | 98 | 2.26 | 615 | 1 major isomer | 1 | 4b |
| I-48 | 1-(3,4-dimethoxyphenyl)-2-[4-[5-[4-[2-(3,4-dimethoxyphenyl)-2-hydroxy-ethoxy]phenyl]-1,2,4-oxadiazol-3-yl]phenoxy]ethanol (isomer 2) | 97.2 | 6.7 | 98 | 2.26 | 615 | 1 major isomer | 1 | 4a |
| I-49 | 1-[3-(difluoromethoxy)-4-methoxy-phenyl]-2-[4-[2-[4-[2-[3- | 94.3 | 9.2 | 99 | 2.76 | 702 | 1 major isomer | 1 | 4a |

-continued

| N° | Name and Isomeric form | Chiral chromatography | | LCUVMS | | | COMMENTS | Scheme | Chiral agent |
|---|---|---|---|---|---|---|---|---|---|
| | | Chiral Purity (%) | Rt(min.) | UV purity (%) | Rt (min.) | m/z | | | |
| | (difluoromethoxy)-4-methoxy-phenyl]-2-hydroxy-ethoxy]phenyl]thiazol-4-yl]phenoxy]ethanol (isomer 2) | | | | | | | | |
| I-50 | 1-[3-(difluoromethoxy)-4-methoxy-phenyl]-2-[4-[2-[4-[2-[3-(difluoromethoxy)-4-methoxy-phenyl]-2-hydroxy-ethoxy]phenyl]thiazol-4-yl]phenoxy]ethanol (isomer 1) | 91.1 | 9.4 | 98.5 | 2.76 | 702 | 1 major isomer | 1 | 4b |
| I-51 | 1-[4-(difluoromethoxy)-3-methoxy-phenyl]-2-[4-[2-[4-[2-[4-(difluoromethoxy)-3-methoxy-phenyl]-2-hydroxy-ethoxy]phenyl]thiazol-4-yl]phenoxy]ethanol (isomer 2) | 72 | 7.6 | 96.6 | 2.8 | 702 | major 1 isomer | 1 | 4a |
| I-52 | 1-[4-(difluoromethoxy)-3-methoxy-phenyl]-2-[4-[2-[4-[2-[4-(difluoromethoxy)-3-methoxy-phenyl]-2-hydroxy-ethoxy]phenyl]thiazol-4-yl]phenoxy]ethanol (isomer 1) | 55.6 | 6.6 | 97.7 | 2.8 | 702 | 1 major isomer | 1 | 4b |

*Purification method: LC preparative chromatography with 2 columns Chiralpak IC (300 × 4.6 mm) 20 µm. Conditions: 100% MeOH - 1 ml/min - 210 nm - 25° C.
**purification method: LC preparative chromatography with Berger Prep SFC (150 × 21 mm 5 µm) UV = 210 nm. Conditions: 2-Ethylpyridine - CO2/Methanol 75%/25% 70 mL/min 100 bar 260 inj de 4.1 mg Some compounds according to the invention underwent biochemical studies in order to demonstrate their capacity to inhibit the mitochondrial complex 1 activity on isolated proteins with a commercial assay according to the protocol described (ab109903: MitoTox Complex 1 OXPHOS Activity Microplate Assay).

In order to evaluate the inhibitory activity of the all compounds, an in vitro assay was developed which read out is directly linked to mitochondrial complex 1 inhibition. Since mitochondrial complex 1 contributes to the formation of membrane potential coupled to the mitochondrial ATP synthesis, complex 1 inhibition directly leads in cells to the inhibition of mitochondrial ATP production. Cellular ATP contents were measured in presence of either glycolysis inhibitor (sodium iodocetate) and/or mitochondrial inhibitors (F0F1-ATPase inhibitor: oligomycin or mitochondrial uncoupler: FCCP) to determine the ATP production part relying either on glycolytic or on mitochondrial metabolism. The compounds according to the invention were evaluated in dose effect in order to demonstrate their capacity to inhibit the mitochondrial ATP production.

Mitochondrial ATP Analysis

The compounds of the invention were evaluated for their ability to inhibit mitochondrial ATP production on non-small cell lung carcinoma cell lines NCI-H460, demonstrated for their oxidative pattern.

Sample Preparation

ATP was measured using the Promega Cell Titer Glo kit and protocol. In summary, 1,000 cells were plated in 40 µL in a 384 well plate. 24 hours later, medium was replaced by 20 µl culture medium in presence of compounds: cells were treated in replicates of five with control (PBS), oligomycin A (10 µg/ml), FCCP (30 µM), or the compounds of the invention in dose effect both alone or in combination with sodium iodoacetate (100 µM). Following a 1-hour incubation, 20 µL of CellTtiter-glo™ reaction mix were added to each well for a final volume of 40 µL. Plates were then analyzed for luminescence with a Perkin Elmer EnVision. By comparing the different conditions, global ATP and percentages of both glycolytic and mitochondrial ATP were determined.

Calculation of Results

The mitochondrial ATP production was calculated as the remaining ATP under iodoacetate treatment minus basal ATP (ATP content under iodoacetate and oligomycin treatment). Inhibitory activity of the compounds on mitochondrial ATP in NCI-H460 cells is expressed as the concentration needed to inhibit 50% of mitochondrial ATP production (IC50, M).

| N° | $IC_{50}$ (mito ATP) M |
|---|---|
| I-1 | 3.53E−07 |
| I-2 | 2.30E−08 |
| I-3 | 8.85E−09 |

| N° | IC$_{50}$ (mito ATP) M |
|---|---|
| I-4 | 1.20E−08 |
| I-5 | 8.27E−06 |
| I-6 | 2.13E−08 |
| I-7 | 2.84E−07 |
| I-8 | 2.06E−09 |
| I-9 | 3.86E−09 |
| I-10 | 1.46E−07 |
| I-11 | 5.57E−07 |
| I-12 | 1.28E−07 |
| I-13 | 6.90E−08 |
| I-14 | 6.79E−07 |
| I-15 | 1.55E−06 |
| I-16 | 3.54E−07 |
| I-17 | 3.96E−06 |
| I-18 | 6.28E−08 |
| I-19 | 2.45E−07 |
| I-20 | 1.42E−06 |
| I-21 | 2.65E−06 |
| I-22 | 1.28E−06 |
| I-23 | 1.97E−07 |
| I-24 | 2.54E−07 |
| I-25 | 1.95E−07 |
| I-26 | 7.32E−09 |
| I-27 | 3.68E−09 |
| I-28 | 4.18E−08 |
| I-29 | 1.59E−07 |
| I-30 | 1.67E−07 |
| I-31 | 3.00E−07 |
| I-32 | 4.76E−08 |
| I-33 | 3.01E−08 |
| I-34 | 6.00E−09 |
| I-35 | 3.03E−07 |
| I-36 | 6.76E−07 |
| I-37 | 9.43E−08 |
| I-38 | 1.33E−07 |
| I-39 | 9.25E−08 |
| I-40 | 2.81E−07 |
| I-41 | 5.39E−07 |
| I-42 | 3.00E−08 |
| I-43 | 3.70E−08 |
| I-44 | 5.44E−08 |
| I-45 | 4.26E−07 |
| I-46 | >10E−06 |
| I-47 | >10E−06 |
| I-48 | >10E−06 |
| I-49 | >10E−06 |
| I-50 | 1.34E−06 |
| I-51 | >10E−06 |
| I-52 | >10E−06 |
| I-53 | 9.56E−07 |
| I-54 | 6.72E−07 |
| I-55 | 4.35E−07 |
| I-56 | 7.60E−07 |
| I-57 | 5.19E−08 |
| I-58 | 4.58E−07 |
| I-59 | 2.75E−06 |
| I-60 | >10E−06 |
| I-61 | 3.26E−07 |
| I-62 | 4.92E−07 |
| I-63 | 4.29E−08 |
| I-64 | 1.80E−07 |
| I-65 | 2.38E−08 |
| I-66 | 2.65E−08 |
| I-67 | 1.56E−07 |
| I-68 | 3.28E−08 |

| N° | Complex I (IC$_{50}$) nM\|$_{[SHP1]}$ |
|---|---|
| I-1 | 257 |
| I-2 | 2.93 |
| I-3 | 3.53 |
| I-4 | 25.7 |
| I-5 | >10 μM |
| I-6 | 13.5 |
| I-8 | 15.6 |
| I-9 | 37.3 |
| I-10 | 196 |
| I-11 | 146 |
| I-12 | 15.7 |
| I-13 | 222 |
| I-14 | 220 |
| I-15 | 1240 |
| I-16 | 839 |
| I-17 | 1710 |
| I-18 | 12.6 |
| I-19 | 2.24 |
| I-20 | 351 |
| I-21 | 602 |
| I-22 | 1280 |
| I-23 | 381 |
| I-24 | 38.2 |
| I-25 | 82.5 |
| I-26 | 4.9 |
| I-27 | 1.4 |
| I-28 | 2.2 |
| I-29 | 61.9 |
| I-30 | 30.0 |
| I-31 | 63.2 |
| I-32 | 6 |
| I-33 | 28.5 |
| I-34 | 26.5 |
| I-35 | 361 |
| I-36 | 335 |
| I-37 | 13.1 |
| I-39 | 35.7 |
| I-40 | 664 |
| I-41 | 281 |
| I-43 | 9.3 |
| I-44 | 12.9 |
| I-45 | 696 |
| I-53 | >1 μM |
| I-54 | 240 |
| I-58 | 239 |
| I-59 | >10 μM |
| I-61 | 44.1 |
| I-62 | 135 |
| I-63 | 29.2 |
| I-64 | 39.0 |
| I-65 | 16.2 |
| I-66 | 24.4 |
| I-67 | 51.4 |
| I-68 | 52.6 |

The IC50 values are generally below $10^{-06}$ M, and more particularly between $2.6 \cdot 10^{-9}$ M and $8.3 \cdot 10^{-6}$ M for ATP and are generally below $10^{-06}$ M, and more particularly between 1.4 and 1710 nM for Complex 1.

Other tests involving the in vitro activity of the compounds of the invention were carried out.

Since it was sought to determine the efficacy of the compounds to inhibit HIF1a stabilization under hypoxia, the compounds according to the invention underwent biochemical studies in order to determine their capacity to decrease HIF stabilization in Hep3b cells under hypoxia (western blot model).

Western Blot Model

Sample Preparation

Hep3B cells are seeded at a rate of 300000 cells per well in 6-wells culture plate in 2 ml of MEM supplemented with glutamin (2 mM) and 10% FCS (foetal calf serum) and incubated at 37° C. in the presence of 5% CO2. The next day, the cells are placed in contact with the compound and an incubation under hypoxia at 1% 02 is carried out at 37° C. in 95% humidity and 5% CO2 in a sealed anaerobic workstation (Hypoxystation H35—Don Whitley—AES Chemunex) during 6 hours.

Immunoblotting

Cells were washed (PBS) and lysed in SDS sample buffer. Proteins (25 μg) were separated on 4-12% Bis-Tris gels and transferred onto polyvinylidene difluoride membranes (Millipore). Membranes were blotted with a mouse monoclonal antibody to HIF-1a (BD transduction) and a mouse monoclonal anti-βactin (Sigma). Immunoreactive bands were detected with a horse radish peroxydase (HRP) anti-mouse antibody (Sigma) by enhanced chemiluminescence (Promega).

Calculation of Results

The inhibitory activity of the compounds for their capacity to decrease HIF1-a stabilization in Hep3b under hypoxia is expressed as range of percentage relative to control with:

| N° | Western Blot | |
|---|---|---|
| I-1 | 48 | * |
| I-2 | 54 | ** |
| I-3 | 70 | *** |
| I-4 | 72 | *** |
| I-6 | 43 | * |
| I-7 | 63 | ** |
| I-8 | 47 | * |
| I-9 | 58.5 | ** |
| I-10 | 62 | ** |
| I-11 | 65 | ** |
| I-12 | 38 | * |
| I-13 | 51 | ** |
| I-14 | 59 | ** |
| I-18 | 71 | *** |
| I-19 | 56 | ** |
| I-21 | 52 | ** |
| I-22 | 57 | ** |
| I-24 | 49 | * |
| I-25 | 41 | * |
| I-26 | 39 | * |
| I-27 | 40 | * |
| I-29 | 67 | ** |
| I-30 | 56 | ** |
| I-31 | 64 | ** |
| I-32 | 45 | * |
| I-33 | 52 | * |
| I-34 | 64 | ** |
| I-35 | 68 | ** |
| I-36 | 62 | ** |
| I-37 | 74 | *** |
| I-38 | 79 | *** |
| I-39 | 51 | ** |
| I-42 | 56 | ** |
| I-43 | 32 | * |
| I-44 | 45 | * |
| I-45 | 87 | *** |
| I-47 | 51 | ** |
| I-48 | 87 | *** |
| I-55 | 62 | ** |
| I-56 | 75 | *** |
| I-57 | 18 | – |
| I-58 | 56 | ** |
| I-61 | 46 | * |
| I-62 | 43 | * |
| I-63 | 64 | ** |
| I-64 | 58 | ** |
| I-65 | 41 | * |
| I-66 | 54 | ** |

– represents a decrease of HIF1-a stabilization is less than 30%
* represents a decrease of HIF-a stabilization between 30 to 50%
** represents a decrease of HIF-a stabilization between 50 to 70%
*** represents a decrease of HIF-a stabilization higher than 70%

Most of the compounds induced a decrease of HIF1-a stabilization of at least 30%.

It is therefore apparent that the compounds of the invention have an inhibitory activity for the complex 1 of the mitochondrial respiratory chain and for HIF1-a.

The compounds according to the invention can therefore be used for preparing medicaments, especially medicaments which are inhibitors of the complex 1 of the mitochondrial respiratory chain.

Accordingly, in another of its aspects, the invention provides medicaments which comprise a compound of formula (I), or an addition salt thereof with a pharmaceutically acceptable acid of the compound of formula (I).

These medicaments are employed therapeutically, especially in the treatment and prevention of cancer, in particular carcinomas which have a metabolism dependent on oxidative phosphorylation, such as lung tumors and more specifically non-small cell lung cancers, hormono-dependent breast tumors, ovarian tumors, hepatocarcinomas, gastrointestinal, pancreatic, and colon tumors, overexpressing c-Myc tumor such as lymphomas, breast or colon cancer, well to medium differentiated tumors, cancers which induce primary lymph node and lung metastases, early grades of cancers described to present hypoxic regions during their development and metabolic adaptation (glycolytic shift) such as melanomas, gliomas, head and neck carcinomas, leukemias.

According to another of its aspects, the present invention relates to pharmaceutical compositions comprising as active principle a compound according to the invention. These pharmaceutical compositions comprise an effective dose of at least one compound according to the invention, or a pharmaceutically acceptable salt of the said compound, and also at least one pharmaceutically acceptable excipient.

The said excipients are selected, in accordance with the pharmaceutical form and method of administration desired, from the customary excipients, which are known to a person skilled in the art.

In the pharmaceutical compositions of the present invention for oral, sublingual, subcutaneous, intramuscular, intravenous, topical, local, intra-tracheal, intranasal, transdermal or rectal administration, the active principle of formula (I) above, or its salt, may be administered in a unit administration form, in a mixture with conventional pharmaceutical excipients, to animals and to human beings for the treatment of the above disorders or diseases.

The unit administration forms appropriate include oral forms such as tablets, soft or hard gel capsules, powders, granules and oral solutions or suspensions, sublingual, buccal, intratracheal, intra-ocular and intranasal administration forms, forms for inhalative, topical, transdermal, subcutaneous, intra-muscular or intravenous administration, rectal administration forms and implants. For topical application it is possible to use the compounds according to the invention in creams, gels, ointments or lotions.

As an example, a unit administration form of a compound according to the invention in tablet form may comprise the following components:

| | |
|---|---|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

The present invention, according to another of its aspects, also provides a method of treating the pathologies indicated above, which comprises administering to a patient an effective dose of a compound according to the invention, or one of its pharmaceutically acceptable salts.

The invention claimed is:

1. A compound of formula (I)

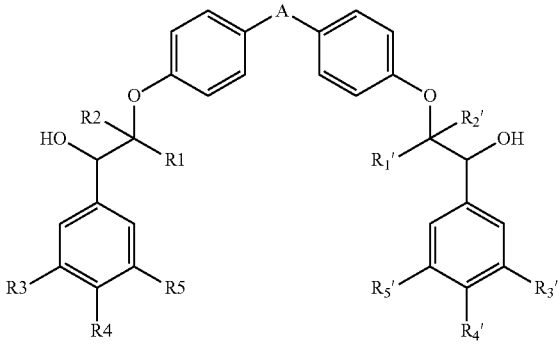

wherein:
A is a 5-membered heteroaryl group comprising between 1 and 3 heteroatoms,
   wherein at least one heteroatom is selected from the group consisting of a sulfur atom and a nitrogen atom,
   wherein A is unsubstituted or substituted with one or more (C1-C4)alkyl groups, and
   wherein each (C1-C4) alkyl group is unsubstituted or substituted with a heterocyclyl group;
each R1, R2, $R_1'$ and $R_2'$ is independently a hydrogen atom or a (C1-C4 alkyl) group; and
each R3, R4, R5, $R_3'$, $R_4'$ and $R_5'$ is independently selected from the group consisting of a hydrogen atom, a halogen atom, an —O-fluoromethyl group and a (C1-C4)alkoxy group,
   wherein at least one of R3, R4 and R5 is a (C1-C4) alkoxy group, and
   wherein at least one of $R_3'$, $R_4'$ and $R_5'$ is a (C1-C4) alkoxy group,
in the form of a base, an enantiomer, a diastereomer, or an acid addition salt.

2. The compound of claim 1, in the form of a base, an enantiomer, a diastereomer, or an acid addition salt, wherein A is an oxazolyl, thiazol, thienyl, oxadiazolyl, thiadiazolyl or imidazolyl group.

3. The compound of claim 1, in the form of a base, an enantiomer, a diastereomer, or an acid addition salt, wherein A is unsubstituted.

4. The compound of claim 1, in the form of a base, an enantiomer, a diastereomer, or an acid addition salt, wherein A is substituted with one or more methyl groups.

5. The compound of claim 1, in the form of a base, an enantiomer, a diastereomer, or an acid addition salt, wherein each of R1, R2, $R_1'$ and $R_2'$ is a hydrogen atom or a methyl group.

6. The compound of claim 5, in the form of a base, an enantiomer, a diastereomer, or an acid addition salt, wherein each of R1, R2, $R_1'$ and $R_2'$ is a hydrogen atom.

7. The compound of claim 1, in the form of a base, an enantiomer, a diastereomer, or an acid addition salt, wherein at least two of R3, R4 and R5 are —OCH$_3$ and at least two of $R_3'$, $R_4'$ and $R_5'$ are —OCH$_3$.

8. The compound of claim 7, in the form of a base, an enantiomer, a diastereomer, or an acid addition salt, wherein two of R3, R4 and R5 are —OCH$_3$ and two of $R_3'$, $R_4'$ and $R_5'$ are —OCH$_3$.

9. The compound of claim 1, in the form of a base, an enantiomer, a diastereomer, or an acid addition salt, wherein at least one of R3, R4, R5, $R_3'$, $R_4'$ and $R_5'$ is —OCHF$_2$.

10. The compound of claim 1, in the form of a base, an enantiomer, a diastereomer, or an acid addition salt, wherein R1 is $R_1'$, R2 is $R_2'$, R3 is $R_3'$, R4 is $R_4'$, and R5 is $R_5'$.

11. The compound of claim 1, in the form of a base, an enantiomer, a diastereomer, or an acid addition salt, which is selected from the group consisting of:
   1-(3,4-dimethoxyphenyl)-2-[4-[2-[4-[2-(3,4-dimethoxyphenyl)-2-hydroxy-ethoxy]phenyl]-5-methyl-oxazol-4-yl]phenoxy]ethanol;
   1-(3,4-dimethoxyphenyl)-2-[4-[2-[4-[2-(3,4-dimethoxyphenyl)-2-hydroxy-1,1-dimethyl-ethoxy]phenyl]-5-methyl-oxazol-4-yl]phenoxy]-2-methyl-propan-1-ol;
   1-(3,4-dimethoxyphenyl)-2-[4-[2-[4-[2-(3,4-dimethoxyphenyl)-2-hydroxy-ethoxy]phenyl]-4-methyl-oxazol-5-yl]phenoxy]ethanol;
   1-(3,4-dimethoxyphenyl)-2-[4-[2-[4-[2-(3,4-dimethoxyphenyl)-2-hydroxy-1,1-dimethyl-ethoxy]phenyl]-5-methyl-thiazol-4-yl]phenoxy]-2-methyl-propan-1-ol;
   1-(3,4-dimethoxyphenyl)-2-[4-[2-[4-[2-(3,4-dimethoxyphenyl)-2-hydroxy-ethoxy]phenyl]-5-methyl-thiazol-4-yl]phenoxy]ethanol;
   1-(3,4-dimethoxyphenyl)-2-[4-[2-[4-[2-(3,4-dimethoxyphenyl)-2-hydroxy-1,1-dimethyl-ethoxy]phenyl]-5-methyl-thiazol-4-yl]phenoxy]-2-methyl-propan-1-ol;
   1-(3,4-dimethoxyphenyl)-2-[4-[2-[4-[2-(3,4-dimethoxyphenyl)-2-hydroxy-ethoxy]phenyl]-5-methyl-thiazol-4-yl]phenoxy]ethanol;
   1-(3,4-dimethoxyphenyl)-2-[4-[2-[4-[2-(3,4-dimethoxyphenyl)-2-hydroxy-1-methyl-ethoxy]phenyl]oxazol-4-yl]phenoxy]propan-1-ol;
   1-(3,4-dimethoxyphenyl)-2-[4-[2-[4-[2-(3,4-dimethoxyphenyl)-2-hydroxy-ethoxy]phenyl]oxazol-4-yl]phenoxy]ethanol;
   1-(4-chloro-3-methoxy-phenyl)-2-[4-[2-[4-[2-(4-chloro-3-methoxy-phenyl)-2-hydroxy-ethoxy]phenyl]oxazol-4-yl]phenoxy]ethanol;
   1-(4-fluoro-3-methoxy-phenyl)-2-[4-[2-[4-[2-(4-fluoro-3-methoxy-phenyl)-2-hydroxy-ethoxy]phenyl]oxazol-4-yl]phenoxy]ethanol;
   1-(3-fluoro-4-methoxy-phenyl)-2-[4-[2-[4-[2-(3-fluoro-4-methoxy-phenyl)-2-hydroxy-ethoxy]phenyl]oxazol-4-yl]phenoxy]ethanol;
   1-(3,4-dimethoxyphenyl)-2-[4-[2-[4-[2-(3,4-dimethoxyphenyl)-2-hydroxy-1,1-dimethyl-ethoxy]phenyl]oxazol-4-yl]phenoxy]-2-methyl-propan-1-ol;
   2-[4-[2-[4-[2-hydroxy-2-(3,4,5-trimethoxyphenyl)ethoxy]phenyl]oxazol-4-yl]phenoxy]-1-(3,4,5-trimethoxyphenyl)ethanol;
   1-(3,4-dimethoxyphenyl)-2-[4-[2-[4-[2-(3,4-dimethoxyphenyl)-2-hydroxy-ethoxy]phenyl]thiazol-4-yl]phenoxy]ethanol;
   1-(3,4-dimethoxyphenyl)-2-[4-[2-[4-[2-(3,4-dimethoxyphenyl)-2-hydroxy-1,1-dimethyl-ethoxy]phenyl]thiazol-4-yl]phenoxy]-2-methyl-propan-1-ol;
   1-(3,4-dimethoxyphenyl)-2-[4-[2-[4-[2-(3,4-dimethoxyphenyl)-2-hydroxy-1-methyl-ethoxy]phenyl]thiazol-4-yl]phenoxy]propan-1-ol;
   1-(3,4-dimethoxyphenyl)-2-[4-[2-[4-[2-(3,4-dimethoxyphenyl)-2-hydroxy-ethoxy]phenyl]thiazol-4-yl]phenoxy]ethanol;
   1-(3,4-dimethoxyphenyl)-2-[4-[4-[4-[2-(3,4-dimethoxyphenyl)-2-hydroxy-ethoxy]phenyl]thiazol-2-yl]phenoxy]-2-methyl-propan-1-ol;

1-(3,4-dimethoxyphenyl)-2-[4-[2-[4-[2-(3,4-dimethoxy-phenyl)-2-hydroxy-ethoxy]phenyl]thiazol-4-yl]phenoxy]-2-methyl-propan-1-ol;
1-(3,4-dimethoxyphenyl)-2-[4-[5-[4-[2-(3,4-dimethoxy-phenyl)-2-hydroxy-1,1-dimethyl-ethoxy]phenyl]-3-thienyl]phenoxy]-2-methyl-propan-1-ol;
1-(3,4-dimethoxyphenyl)-2-[4-[5-[4-[2-(3,4-dimethoxy-phenyl)-2-hydroxy-ethoxy]phenyl]-3-thienyl]phenoxy]ethanol;
1-(3,4-dimethoxyphenyl)-2-[4-[5-[4-[2-(3,4-dimethoxy-phenyl)-2-hydroxy-ethoxy]phenyl]-1,2,4-oxadiazol-3-yl]phenoxy]ethanol;
1-(3,4-dimethoxyphenyl)-2-[4-[5-[4-[2-(3,4-dimethoxy-phenyl)-2-hydroxy-1,1-dimethyl-ethoxy]phenyl]-1,2,4-oxadiazol-3-yl]phenoxy]-2-methyl-propan-1-ol;
1-(3,4-dimethoxyphenyl)-2-[4-[5-[4-[2-(3,4-dimethoxy-phenyl)-2-hydroxy-1-methyl-ethoxy]phenyl]-1,2,4-thiadiazol-3-yl]phenoxy]propan-1-ol;
1-(3,4-dimethoxyphenyl)-2-[4-[5-[4-[2-(3,4-dimethoxy-phenyl)-2-hydroxy-ethoxy]phenyl]-1,2,4-thiadiazol-3-yl]phenoxy]ethanol;
1-(3,4-dimethoxyphenyl)-2-[4-[5-[4-[2-(3,4-dimethoxy-phenyl)-2-hydroxy-1,1-dimethyl-ethoxy]phenyl]-1,2,4-thiadiazol-3-yl]phenoxy]-2-methyl-propan-1-ol;
1-(3,4-dimethoxyphenyl)-2-[4-[5-[4-[2-(3,4-dimethoxy-phenyl)-2-hydroxy-1,1-dimethyl-ethoxy]phenyl]-1,2,4-thiadiazol-3-yl]phenoxy]-2-methyl-propan-1-ol;
1-(3,4-dimethoxyphenyl)-2-[4-[2-[4-[2-(3,4-dimethoxy-phenyl)-2-hydroxy-1-methyl-ethoxy]phenyl]oxazol-5-yl]phenoxy]propan-1-ol;
1-(3,4-dimethoxyphenyl)-2-[4-[2-[4-[2-(3,4-dimethoxy-phenyl)-2-hydroxy-ethoxy]phenyl]-1H-imidazol-4-yl]phenoxy]ethanol;
1-(3,4-dimethoxyphenyl)-2-[4-[2-[4-[2-(3,4-dimethoxy-phenyl)-2-hydroxy-1,1-dimethyl-ethoxy]phenyl]-1H-imidazol-4-yl]phenoxy]-2-methyl-propan-1-ol;
1-(3,4-dimethoxyphenyl)-2-[4-[2-[4-[2-(3,4-dimethoxy-phenyl)-2-hydroxy-1,1-dimethyl-ethoxy]phenyl]-1-methyl-imidazol-4-yl]phenoxy]-2-methyl-propan-1-ol;
1-(3,4-dimethoxyphenyl)-2-[4-[2-[4-[2-(3,4-dimethoxy-phenyl)-2-hydroxy-ethoxy]phenyl]-1-methyl-imidazol-4-yl]phenoxy]ethanol;
1-(3,4-dimethoxyphenyl)-2-[4-[2-[4-[2-(3,4-dimethoxy-phenyl)-2-hydroxy-1,1-dimethyl-ethoxy]phenyl]-1-(2-morpholinoethyl)imidazol-4-yl]phenoxy]-2-methyl-propan-1-ol;
1-(3,4-dimethoxyphenyl)-2-[4-[2-[4-[2-(3,4-dimethoxy-phenyl)-2-hydroxy-ethoxy]phenyl]-1-(2-morpholino-ethyl)imidazol-4-yl]phenoxy]ethanol;
1-(3,4-dimethoxyphenyl)-2-[4-[2-[4-[2-(3,4-dimethoxy-phenyl)-2-hydroxy-ethoxy]phenyl]-4-methyl-oxazol-5-yl]phenoxy]ethanol;
1-(3,4-dimethoxyphenyl)-2-[4-[5-[4-[2-(3,4-dimethoxy-phenyl)-2-hydroxy-ethoxy]phenyl]-1,2,4-oxadiazol-3-yl]phenoxy]ethanol;
1-[3-(difluoromethoxy)-4-methoxy-phenyl]-2-[4-[2-[4-[2-[3-(difluoromethoxy)-4-methoxy-phenyl]-2-hydroxy-ethoxy]phenyl]thiazol-4-yl]phenoxy]ethanol; and
1-[4-(difluoromethoxy)-3-methoxy-phenyl]-2-[4-[2-[4-[2-[4-(difluoromethoxy)-3-methoxy-phenyl]-2-hydroxy-ethoxy]phenyl]thiazol-4-yl]phenoxy]ethanol.

12. A process for preparing the compound of claim 1, comprising reducing a compound of formula (II)

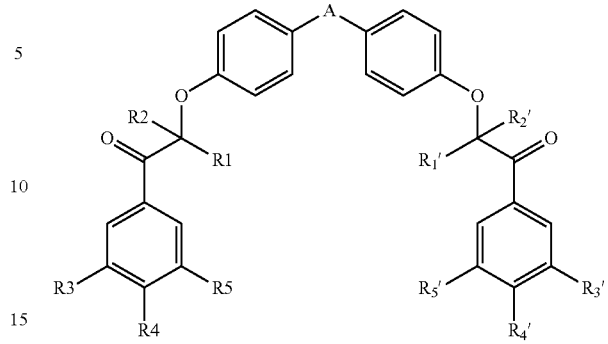

wherein A, R1, R2, R3, R4, R5, $R_1'$, $R_2'$, $R_3'$, $R_4'$ and $R_5'$ have the same meanings as in claim 1, to give the compound of claim 1.

13. A process for preparing the compound of claim 1, comprising reducing a compound of formula (III):

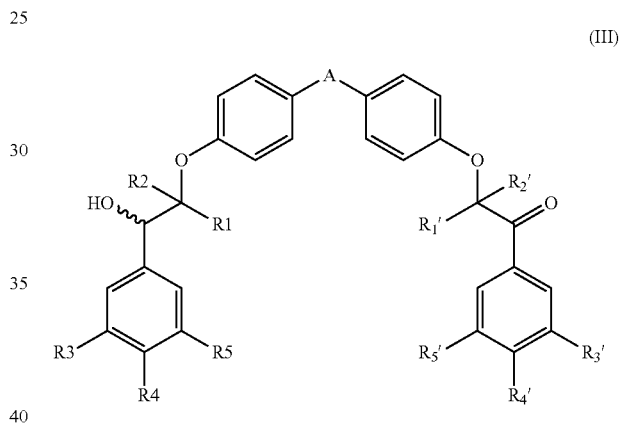

wherein A, R1, R2, R3, R4, R5, $R_1'$, $R_2'$, $R_3'$, $R_4'$ and $R_5'$ have the same meanings as in claim 1, to give the compound of claim 1.

14. A compound of formula (II)

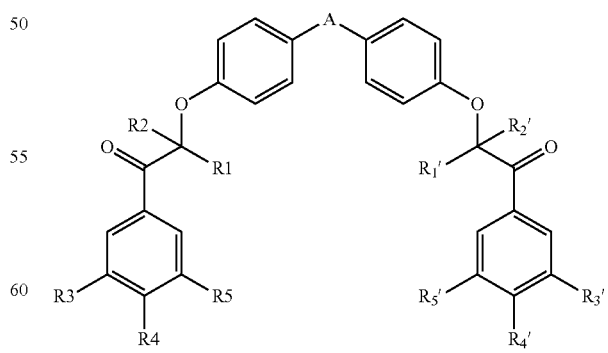

wherein:
A is a 5-membered heteroaryl group comprising between 1 and 3 heteroatoms, wherein at least one heteroatom is selected from the group consisting of a sulfur atom and a nitrogen atom,
wherein A is unsubstituted or substituted with one or more (C1-C4)alkyl groups, and
wherein each (C1-C4) alkyl group is unsubstituted or substituted with a heterocyclyl group;
each R1, R2, $R_1'$ and $R_2'$ is independently a hydrogen atom or a (C1-C4 alkyl) group; and
each R3, R4, R5, $R_3'$, $R_4'$ and $R_5'$ is independently selected from the group consisting of a hydrogen atom, a halogen atom, an —O-fluoromethyl group and a (C1-C4)alkoxy group,
wherein at least one of R3, R4 and R5 is a (C1-C4) alkoxy group, and
wherein at least one of $R_3'$, $R_4'$ and $R_5'$ is a (C1-C4) alkoxy group.

15. A compound of formula (III)

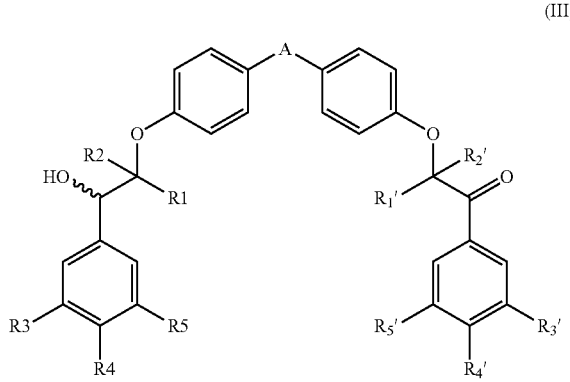

(III)

wherein:
A is a 5-membered heteroaryl group comprising between 1 and 3 heteroatoms,
wherein at least one heteroatom is selected from the group consisting of a sulfur atom and a nitrogen atom,
wherein A is unsubstituted or substituted with one or more (C1-C4)alkyl groups, and
wherein each (C1-C4) alkyl group is unsubstituted or substituted with a heterocyclyl group;
each R1, R2, $R_1'$ and $R_2'$ is independently a hydrogen atom or a (C1-C4 alkyl) group; and
each R3, R4, R5, $R_3'$, $R_4'$ and $R_5'$ is independently selected from the group consisting of a hydrogen atom, a halogen atom, an —O-fluoromethyl group and a (C1-C4)alkoxy group,
wherein at least one of R3, R4 and R5 is a (C1-C4) alkoxy group, and
wherein at least one of $R_3'$, $R_4'$ and $R_5'$ is a (C1-C4) alkoxy group.

16. A pharmaceutical composition comprising the compound of claim 1, or a pharmaceutically acceptable salt thereof, and at least one pharmaceutically acceptable excipient.

17. A method of inhibiting complex 1 of the mitochondrial respiratory chain comprising contacting complex 1 of the mitochondrial respiratory chain with the compound of claim 1, in the form of a base, an enantiomer, a diastereomer, or an acid addition salt.

18. A method of treating cancer in a patient in need thereof comprising administering to the patient a therapeutically effective amount of the compound of claim 1, in the form of a base, an enantiomer, a diastereomer, or an acid addition salt.

19. The method of claim 18, wherein the cancer is selected from the group consisting of carcinomas which have a metabolism dependent on oxidative phosphorylation, overexpressing c-Myc tumor, well to medium differentiated tumors, cancers which induce primary lymph node and lung metastases, and early grades of cancers described to present hypoxic regions during their development and metabolic adaptation (glycolytic shift).

20. The method of claim 19, wherein the cancer is selected from the group consisting of lung tumors, hormone-dependent breast tumors, ovarian tumors, hepatocarcinomas, gastrointestinal tumors, pancreatic tumors, and colon tumors.

21. The method of claim 19, wherein the cancer is non-small cell lung cancer.

22. The method of claim 19, wherein the cancer is selected from the group consisting of lymphomas, breast cancer, and colon cancer.

23. The method of claim 19, wherein the cancer is selected from the group consisting of melanomas, gliomas, head and neck carcinomas, and leukemias.

* * * * *